US011046754B2

(12) United States Patent
Chao

(10) Patent No.: US 11,046,754 B2
(45) Date of Patent: Jun. 29, 2021

(54) DENGUE VIRUS-LIKE PARTICLE, ANTIBODY AGAINST DENGUE VIRUS, AND COMPOSITION COMPRISING THE SAME

(71) Applicant: Day-Yu Chao, Taipei (TW)

(72) Inventor: Day-Yu Chao, Taipei (TW)

(73) Assignee: DAY-YU CHAO, Taipei (TW)

( * ) Notice: Subject to any disclaimer, the term of this patent is extended or adjusted under 35 U.S.C. 154(b) by 0 days.

(21) Appl. No.: 16/345,558

(22) PCT Filed: Oct. 26, 2017

(86) PCT No.: PCT/CN2017/107743
§ 371 (c)(1),
(2) Date: Apr. 26, 2019

(87) PCT Pub. No.: WO2018/077208
PCT Pub. Date: May 3, 2018

(65) Prior Publication Data
US 2019/0315839 A1    Oct. 17, 2019

Related U.S. Application Data

(60) Provisional application No. 62/413,597, filed on Oct. 27, 2016.

(51) Int. Cl.
*A61K 39/12*         (2006.01)
*C07K 14/005*       (2006.01)
*C07K 16/10*         (2006.01)
*A61K 39/00*         (2006.01)

(52) U.S. Cl.
CPC .......... *C07K 16/1081* (2013.01); *A61K 39/12* (2013.01); *C07K 14/005* (2013.01); *A61K 2039/5258* (2013.01); *C07K 2317/76* (2013.01); *C12N 2770/24122* (2013.01); *C12N 2770/24123* (2013.01); *C12N 2770/24134* (2013.01)

(58) Field of Classification Search
None
See application file for complete search history.

(56) References Cited

U.S. PATENT DOCUMENTS

2015/0225474 A1    8/2015    Robinson et al.

FOREIGN PATENT DOCUMENTS

| CN | 1249781 A | 4/2000 |
|---|---|---|
| WO | WO 2010/043977 A2 | 4/2010 |
| WO | WO 2011/146933 A3 | 11/2011 |
| WO | WO 2013/009884 A1 | 1/2013 |
| WO | WO 2014/210358 A1 | 12/2014 |
| WO | WO 2016/148653 A1 | 9/2016 |

OTHER PUBLICATIONS

Aaskov et al., "Serologically defined linear epitopes in the envelope protein of dengue 2 (Jamaica strain 1409)," Arch Virol, vol. 105, 1989, pp. 209-221.
Allison et al., "Synthesis and Secretion of Recombinant Tick-Borne Encephalitis Virus Protein E in Soluble and Particulate Form," Journal of Virology, vol. 69, No. 9, Sep. 1995, pp. 5816-5820.
Bhatt et al., "The global distribution and burden of dengue," Nature, vol. 496, Apr. 25, 2013 (published online Apr. 7, 2013), pp. 504-507.
Chambers et al., "Production of Yellow Fever Virus Proteins in Infected Cells: Identification of Discrete Polyprotein Species and Analysis of Cleavage Kinetics Using Region-Specific Polyclonal Antisera," Virology, vol. 177, 1990, pp. 159-174.
Crabtree et al., "Genetic and phenotypic characterization of the newly described insect flavivirus, Kamiti River virus," Arch Virol, vol. 148, 2003 (published online Apr. 9, 2003), pp. 1095-1118.
Crill et al., "Humoral Immune Responses of Dengue Fever Patients Using Epitope-Specific Serotype-2 Virus-like Particle Antigens," PLoS ONE, vol. 4, Issue 4, e4991, Apr. 1, 2009, pp. 1-18.
Dejnirattisai et al., "A new class of highly potent, broadly neutralizing antibodies isolated from viremic patients infected with dengue virus," Nature Immunology, vol. 16, No. 2, Feb. 2015 (published online Dec. 15, 2014), pp. 170-177 (12 pages total).
Dejnirattisai et al., "Cross-Reacting Antibodies Enhance Dengue Virus Infection in Humans," Science, vol. 328, May 7, 2010, pp. 745-748 (6 pages total).
Ferlenghi et al., "Molecular Organization of a Recombinant Subviral Particle from Tick-Borne Encephalitis Virus," Molecular Cell, vol. 7, Mar. 2001, pp. 593-602.
Fibriansah et al., "Cryo-EM structure of an antibody that neutralizes dengue virus type 2 by locking E protein dimers," Science, vol. 349, Issue 6243, Jul. 3, 2015, pp. 88-91 (5 pages total).
Guy et al., "Dengue vaccine: hypotheses to understand CYD-TDV-induced protection," Nature Reviews—Microbiology, vol. 14, Jan. 2016 (published online Dec. 7, 2015), pp. 45-54.
Junjhon et al., "Differential Modulation of prM Cleavage, Extracellular Particle Distribution, and Virus Infectivity by Conserved Residues at Nonfurin Consensus Positions of the Dengue Virus pr-M Junction," Journal of Virology, vol. 82, No. 21, Nov. 2008 (published ahead of print Aug. 20, 2008), pp. 10776-10791.
Junjhon et al., "Influence of pr-M Cleavage on the Heterogeneity of Extracellular Dengue Virus Particles," Journal of Virology, vol. 84, No. 16, Aug. 2010 (published ahead of print Jun. 2, 2010), pp. 8353-8358.
Keelapang et al., "Alterations of pr-M Cleavage and Virus Export in pr-M Junction Chimeric Dengue Viruses," Journal of Virology, vol. 78, No. 5, Mar. 2004, pp. 2367-2381.

(Continued)

*Primary Examiner* — Benjamin P Blumel
(74) *Attorney, Agent, or Firm* — Birch, Stewart, Kolasch & Birch, LLP

(57) ABSTRACT

The present invention is related to a Dengue virus-like particle. Said Dengue virus-like particle exhibits almost-cut pr-M junction and is particularly suitable for producing antibody that recognizes all four types of Dengue virus. The present invention also provides antibody obtained by using said virus-like particle and composition comprising the same.

9 Claims, 10 Drawing Sheets
Specification includes a Sequence Listing.

(56) References Cited

OTHER PUBLICATIONS

Kostyuchenko et al., "Immature and Mature Dengue Serotype 1 Virus Structures Provide Insight into the Maturation Process," Journal of Virology, vol. 87, No. 13, Jul. 2013 (published ahead of print May 1, 2013), pp. 7700-7707.
Kuhn et al., "Structure of Dengue Virus: Implications for Flavivirus Organization, Maturation, and Fusion," Cell, vol. 108, Mar. 8, 2002, pp. 717-725.
Lok et al., "Binding of a neutralizing antibody to dengue virus alters the arrangement of surface glycoproteins," Nature Structural & Molecular Biology, vol. 15, No. 3, Mar. 2008 (published online Feb. 10, 2008), pp. 312-317.
Nelson et al., "Maturation of West Nile Virus Modulates Sensitivity to Antibody-Mediated Neutralization," PLoS Pathogens, vol. 4, Issue 5, e1000060, May 9, 2008, pp. 1-10.
Pierson et al., "Degrees of maturity: the complex structure and biology of flaviviruses," Current Opinion in Virology, vol. 2, 2012, pp. 168-175.
Rodenhuis-Zybert et al., "Immature Dengue Virus: A Veiled Pathogen?" PLoS Pathogens, vol. 6, Issue 1, e1000718, Jan. 8, 2010, pp. 1-9.
Rouvinski et al., "Recognition determinants of broadly neutralizing human antibodies against dengue viruses," Nature, vol. 520, Apr. 2, 2015 (published online Jan. 12, 2015), pp. 109-113 (16 pages total).
Schalich et al., "Recombinant Subviral Particles from Tick-Borne Encephalitis Virus Are Fusogenic and Provide a Model System for Studying Flavivirus Envelope Glycoprotein Functions," Journal of Virology, vol. 70, No. 7, Jul. 1996, pp. 4549-4557.
Tian et al., "Computational prediction of furin cleavage sites by a hybrid method and understanding mechanism underlying diseases," Scientific Reports, vol. 2, No. 261, Feb. 16, 2012, pp. 1-7.
Tsai et al., "High-Avidity and Potently Neutralizing Cross-Reactive Human Monoclonal Antibodies Derived from Secondary Dengue Virus Infection," Journal of Virology, vol. 87, No. 23, Dec. 2013 (published ahead of print Sep. 11, 2013), pp. 12562-12575.
Wang et al., "Obstruction of Dengue Virus Maturation by Fab Fragments of the 2H2 Antibody," Journal of Virology, vol. 87, No. 16, Aug. 2013 (published ahead of print Jun. 5, 2013), pp. 8909-8915.
Wilder-Smith et al., "Dengue vaccines at a crossroad," Science, vol. 350, Issue 6261, Nov. 6, 2015, pp. 626-627 (3 pages total).
Zhang et al., "Cryo-EM structure of the mature dengue virus at 3.5-Å resolution," Nature Structural & Molecular Biology, vol. 20, No. 1, Jan. 2013 (published online Dec. 16, 2012), pp. 105-110 (7 pages total).
International Search Report, issued in PCT/CN2017/107743, dated Jan. 29, 2018.
Written Opinion of the International Searching Authority, issued in PCT/CN2017/107743, dated Jan. 29, 2018.
Brett D. Lindenbach and Charles M. Rice, Chapter 32 Flaviviridae: The Viruses and Their Replication, 42 pages.
Edeling et al., "Potent Dengue Virus Neutralization by a Therapeutic Antibody with Low Monovalent Affinity Requires Bivalent Engagement", PLOS, vol. 10, issue 4, Apr. 2014, pp. 1-11.
Li et al., "The Flavivirus Precursor Membrane-Envelope Protein Complex: Structure and Maturation", Science, vol. 319, Mar. 28, 2008, pp. 1830-1834 (6 pages total).
Lindenbach et al., "Flaviviridae: The Viruses and Their Replication", Fields Virology, 5th Edition, 2007, pp. 1101-1152.
Poggainella et al., "Dengue E Protein Domain III-Based DNA Immunisation Induces Strong Antibody Responses to All Four Viral Serotypes", PLOS, Jul. 28, 2015, pp. 1-28.
Robinson et al., "Structure-Guided Design of an Anti-dengue Antibody Directed to a Non-immunodominant Epitope", Cell 162, Jul. 30, 2015, pp. 1-12 (13 pages total).
Sukupolvi-Petty et al., "Type- and Subcomplex-Specific Neutralizing Antibodies against Domain III of Dengue Virus Type 2 Envelope Protein Recognize Adjacent Epitopes", Journal of Virology, vol. 81, No. 23, Dec. 2007, pp. 12816-12826 (12 pages total).
Supplementary European Search Report issued in Application No. 17865400.0 dated Aug. 10, 2020.

(E)

(F)

(G)

(H)

```
                           SEQUENCE LISTING

<160> NUMBER OF SEQ ID NOS: 49

<210> SEQ ID NO 1
<211> LENGTH: 14
<212> TYPE: PRT
<213> ORGANISM: Dengue virus

<400> SEQUENCE: 1

Arg Lys Glu Arg Arg His Glu Gly Met Thr Thr Cys Thr Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: peptide

<400> SEQUENCE: 2

Arg Lys Ser Arg Arg His Glu Gly Met Thr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: peptide

<400> SEQUENCE: 3

Arg Lys Ser Arg Arg Arg Glu Gly Met Thr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: peptide

<400> SEQUENCE: 4

Arg Lys Ser Arg Lys Lys Glu Gly Met Thr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: peptide

<400> SEQUENCE: 5

Arg Lys Ser Arg Lys Lys Val Val Met Thr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: peptide

<400> SEQUENCE: 6
```

Arg Lys Ala Arg Arg His Glu Gly Met Thr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: peptide

<400> SEQUENCE: 7

Arg Lys Ala Arg Arg Arg Glu Gly Met Thr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: peptide

<400> SEQUENCE: 8

Arg Lys Ala Arg Lys Lys Glu Gly Met Thr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: peptide

<400> SEQUENCE: 9

Arg Lys Ala Arg Lys Lys Val Val Met Thr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: peptide

<400> SEQUENCE: 10

Arg Arg Ser Arg Arg His Glu Gly Met Thr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: peptide

<400> SEQUENCE: 11

Arg Arg Ser Arg Arg Arg Glu Gly Met Thr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: peptide

<400> SEQUENCE: 12

Arg Arg Ser Arg Lys Lys Glu Gly Met Thr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: peptide

<400> SEQUENCE: 13

Arg Arg Ser Arg Lys Lys Val Val Met Thr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: peptide

<400> SEQUENCE: 14

Arg Arg Ala Arg Arg His Glu Gly Met Thr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: peptide

<400> SEQUENCE: 15

Thr Ser Glu Arg Arg His Glu Gly Met Thr
1               5                   10

<210> SEQ ID NO 16
<211> LENGTH: 5020
<212> TYPE: DNA
<213> ORGANISM: Artificial Sequence
<220> FEATURE:
<223> OTHER INFORMATION: plasmid

<400> SEQUENCE: 16

| | | | | | |
|---|---|---|---|---|---|
| gactcttcgc | gatgtacggg | ccagatatac | gcgttgacat | tgattattga | ctagttatta | 60 |
| atagtaatca | attacggggt | cattagttca | tagcccatat | atggagttcc | gcgttacata | 120 |
| acttacggta | atggcccgc | ctggctgacc | gcccaacgac | ccccgcccat | tgacgtcaat | 180 |
| aatgacgtat | gttcccatag | taacgccaat | agggactttc | cattgacgtc | aatgggtgga | 240 |
| ctatttacgg | taaactgccc | acttggcagt | acatcaagtg | tatcatatgc | caagtacgcc | 300 |
| ccctattgac | gtcaatgacg | gtaaatggcc | cgcctggcat | tatgcccagt | acatgacctt | 360 |
| atgggacttt | cctacttggc | agtacatcta | cgtattagtc | atcgctatta | ccatggtgat | 420 |
| gcggttttgg | cagtacatca | atgggcgtgg | atagcggttt | gactcacggg | gatttccaag | 480 |
| tctccacccc | attgacgtca | atgggagttt | gttttggcac | caaaatcaac | gggactttcc | 540 |
| aaaatgtcgt | aacaactccg | ccccattgac | gcaaatgggc | ggtaggcgtg | tacggtggga | 600 |
| ggtctatata | agcagagctc | tctggctaac | tagagaaccc | actgcttact | ggcttatcga | 660 |
| aattaatacg | actcactata | gggagaccca | agctggctag | cgtttaaact | taagcttggt | 720 |
| accgccgccg | ccatgggcaa | gaggtccgcc | ggctcaatca | tgtggctcgc | gagcttggca | 780 |
| gttgtcatag | cttgtgcagg | cgccttccat | ttaaccacac | gtaacggaga | accacacatg | 840 |

```
atcgtcagca gacaagagaa agggaaaagt cttctgttta aaacagagga tggcgtgaac    900
atgtgtaccc tcatggccat ggaccttggt gaattgtgtg aagacacaat cacgtacaag    960
tgtccccttc tcaggcagaa tgagccagaa gacatagact gttggtgcaa ctctacgtcc   1020
acgtgggtaa cttatgggac gtgtaccacc atggtagtaa aaaaaagatc aaaaagatca   1080
gtggcactcg ttccacatgt gggaatggga ctggagacac gaactgaaac atggatgtca   1140
tcagaagggg cctggaaaca tgtccagaga attgaaactt ggatcttgag acatccaggc   1200
ttcaccatga tggcagcaat cctggcatac accataggaa cgacacattt ccaaagagcc   1260
ctgattttca tcttactgac agctgtcact ccttcaatga caatgcgttg cataggaatg   1320
tcaaatagag actttgtgga aggggtttca ggaggaagct gggttgacat agtcttagaa   1380
catgggagct gtgtgacgac gatggcaaaa aacaaaccaa cattggattt tgaactgata   1440
aaaacagaag ccaaacagcc tgccacccta aggaagtact gtatagaggc aaagctaacc   1500
aacacaacaa cagaatctcg ctgcccaaca caaggggaac ccagcctaaa tgaagagcag   1560
gacaaaaggt tcgtctgcaa acactccatg gtagacagag gatggggaaa tggatgtgga   1620
ctatttggaa agggaggcat tgtgacctgt gctatgttca gatgcaaaaa gaacatggaa   1680
ggaaaagttg tgcaaccaga aaacttggaa tacaccattg tgataacacc tcactcaggg   1740
gaagagcatg cagtcggaaa tgacacagga aaacatggca aggaaatcaa aataacacca   1800
cagagttcca tcacagaagc agaattgaca ggttatggca ctgtcacaat ggagtgctct   1860
ccaagaacgg gcctcgactt caatgagatg gtgttgttgc agatgaaaaa taaagcttgg   1920
ctggtgcaca ggcaatggtt cctagacctg ccgttaccat ggttgcccgg agcggacaca   1980
caagggtcaa attggataca gaaagagaca ttggtcactt tcaaaaatcc ccatgcgaag   2040
aaacaggatg ttgttgtttt aggatcccaa gaaggggcca tgcacacagc acttacaggg   2100
gccacagaaa tccaaatgtc atcaggaaac ttactcttca ggacatctc caagtgcagg   2160
ctgagaatgg acaagctaca gctcaaagga atgtcatact ctatgtgcac aggaaagttt   2220
aaagttgtga aggaaatagc agaaacacaa catggaacaa tagttatcag agtgcaatat   2280
gaaggggacg gctctccatg caagatccct tttgagataa tggatttgga aaaaagacat   2340
gtcttaggtc gcctgattac agtcaaccca attgtgacag aaaaagatag cccagtcaac   2400
atagaagcag aacctccatt cggagacagc tacatcatca taggagtaga gccgggacaa   2460
ctgaagctca actggtttaa gaaaggaagc acgctgggca aggccttttc aacaactttg   2520
aagggagctc aaagactggc agcgttgggc gacacagcct gggactttgg ctctattgga   2580
ggggtcttca ctccatagg aaaagccgtt caccaagtgt ttggtggtgc cttcagaaca   2640
ctctttgggg gaatgtcttg gatcacacaa ggggctaatgg gtgccctact gctctggatg   2700
ggcgtcaacg cacgagaccg atcaattgct ttggccttct tagccacagg gggtgtgctc   2760
gtgttcttag cgaccaatgt gcatgcttaa ttagtttgag cggccgctcg agtctagagg   2820
gcccgtttaa acccgctgat cagcctcgac tgtgccttct agttgccagc catctgttgt   2880
ttgcccctcc cccgtgcctt ccttgaccct ggaaggtgcc actcccactg tcctttccta   2940
ataaaatgag gaaattgcat cgcattgtct gagtaggtgt cattctattc tggggggtgg   3000
ggtggggcag gacagcaagg gggaggattg ggaagacaat agcaggcatg ctggggatgc   3060
ggtgggctct atggcttcta ctgggcggtt ttatggacag caagcgaacc ggaattgcca   3120
gctggggcgc cctctggtaa ggttgggaag ccctgcaaag taaactggat ggctttctcg   3180
```

| | |
|---|---|
| ccgccaagga tctgatggcg caggggatca agctctgatc aagagacagg atgaggatcg | 3240 |
| tttcgcatga ttgaacaaga tggattgcac gcaggttctc cggccgcttg ggtggagagg | 3300 |
| ctattcggct atgactgggc acaacagaca atcggctgct ctgatgccgc cgtgttccgg | 3360 |
| ctgtcagcgc aggggcgccc ggttcttttt gtcaagaccg acctgtccgg tgccctgaat | 3420 |
| gaactgcaag acgaggcagc gcggctatcg tggctggcca cgacgggcgt tccttgcgca | 3480 |
| gctgtgctcg acgttgtcac tgaagcggga agggactggc tgctattggg cgaagtgccg | 3540 |
| gggcaggatc tcctgtcatc tcaccttgct cctgccgaga agtatccat catggctgat | 3600 |
| gcaatgcggc ggctgcatac gcttgatccg gctacctgcc cattcgacca ccaagcgaaa | 3660 |
| catcgcatcg agcgagcacg tactcggatg aagccggtc ttgtcgatca ggatgatctg | 3720 |
| gacgaagagc atcaggggct cgcgccagcc gaactgttcg ccaggctcaa ggcgagcatg | 3780 |
| cccgacggcg aggatctcgt cgtgacccat ggcgatgcct gcttgccgaa tatcatggtg | 3840 |
| gaaaatggcc gcttttctgg attcatcgac tgtggccggc tgggtgtggc ggaccgctat | 3900 |
| caggacatag cgttggctac ccgtgatatt gctgaagagc ttggcggcga atgggctgac | 3960 |
| cgcttcctcg tgctttacgg tatcgccgct cccgattcgc agcgcatcgc cttctatcgc | 4020 |
| cttcttgacg agttcttctg aattattaac gcttacaatt tcctgatgcg gtattttctc | 4080 |
| cttacgcatc tgtgcggtat ttcacaccgc atacaggtgg cacttttcgg ggaaatgtgc | 4140 |
| gcggaacccc tatttgttta ttttttctaaa tacattcaaa tatgtatccg ctcatgagac | 4200 |
| aataaccctg ataaatgctt caataatagc acgtgctaaa acttcatttt taatttaaaa | 4260 |
| ggatctaggt gaagatcctt tttgataatc tcatgaccaa aatcccttaa cgtgagtttt | 4320 |
| cgttccactg agcgtcagac cccgtagaaa agatcaaagg atcttcttga gatcctttt | 4380 |
| ttctgcgcgt aatctgctgc ttgcaaacaa aaaaaccacc gctaccagcg gtggtttgtt | 4440 |
| tgccggatca agagctacca actctttttc cgaaggtaac tggcttcagc agagcgcaga | 4500 |
| taccaaatac tgtccttcta gtgtagccgt agttaggcca ccacttcaag aactctgtag | 4560 |
| caccgcctac atacctcgct ctgctaatcc tgttaccagt ggctgctgcc agtggcgata | 4620 |
| agtcgtgtct taccgggttg gactcaagac gatagttacc ggataaggcg cagcggtcgg | 4680 |
| gctgaacggg gggttcgtgc acacagccca gcttggagcg aacgacctac accgaactga | 4740 |
| gatacctaca gcgtgagcta tgagaaagcg ccacgcttcc cgaagggaga aaggcggaca | 4800 |
| ggtatccggt aagcggcagg gtcggaacag gagagcgcac gagggagctt ccaggggaa | 4860 |
| acgcctggta tctttatagt cctgtcgggt ttcgccacct ctgacttgag cgtcgatttt | 4920 |
| tgtgatgctc gtcaggggg cggagcctat ggaaaaacgc cagcaacgcg gcctttttac | 4980 |
| ggttcctggg cttttgctgg ccttttgctc acatgttctt | 5020 |

```
<210> SEQ ID NO 17
<211> LENGTH: 107
<212> TYPE: PRT
<213> ORGANISM: Artificial Sequence
<220> FEATURE:
<223> OTHER INFORMATION: antibody

<400> SEQUENCE: 17

Gly Glu Pro Gly Thr Ser Leu Lys Ile Ser Cys Lys Thr Ser Gly Tyr
1               5                   10                  15

Thr Phe Thr Glu Tyr Thr Met Tyr Trp Val Lys Gln Ser His Gly Lys
            20                  25                  30

Ser Leu Glu Trp Ile Gly Gly Ile Asn Pro Asn Asn Gly Gly Thr Thr
```

```
                    35                  40                  45
Tyr Asn Gln Lys Phe Lys Gly Lys Ala Thr Leu Thr Val Asn Lys Ser
            50                  55                  60

Ser Ser Ile Ala Tyr Met Glu Val Arg Asn Leu Thr Ser Glu Asp Ser
 65                  70                  75                  80

Ala Val Tyr Tyr Cys Val Arg Tyr Gly Gly Tyr Tyr Val Phe Asp Tyr
                85                  90                  95

Trp Gly Gln Gly Thr Thr Leu Thr Val Ser Ser
                100                 105
```

<210> SEQ ID NO 18
<211> LENGTH: 107
<212> TYPE: PRT
<213> ORGANISM: Artificial Sequence
<220> FEATURE:
<223> OTHER INFORMATION: antibody

<400> SEQUENCE: 18

```
Thr Leu Trp Lys Thr Gln Ser Pro Ala Ser Leu Ala Val Ser Leu Gly
 1               5                  10                  15

Gln Arg Ala Thr Ile Ser Tyr Arg Ala Ser Lys Ser Val Ser Thr Ser
                20                  25                  30

Gly Tyr Ser Tyr Met His Trp Asn Gln Gln Lys Pro Gly Gln Pro Pro
            35                  40                  45

Arg Leu Leu Ile Tyr Leu Val Ser Asn Leu Glu Ser Gly Val Pro Ala
         50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                85                  90                  95

Glu Leu Thr Arg Arg Arg Gly Pro Ser Ser Arg
                100                 105
```

<210> SEQ ID NO 19
<211> LENGTH: 8
<212> TYPE: PRT
<213> ORGANISM: Artificial Sequence
<220> FEATURE:
<223> OTHER INFORMATION: peptide

<400> SEQUENCE: 19

```
Gly Tyr Thr Phe Thr Glu Tyr Thr
 1               5
```

<210> SEQ ID NO 20
<211> LENGTH: 9
<212> TYPE: PRT
<213> ORGANISM: Artificial Sequence
<220> FEATURE:
<223> OTHER INFORMATION: peptide

<400> SEQUENCE: 20

```
Ile Asn Pro Asn Asn Gly Gly Thr Thr
 1               5
```

<210> SEQ ID NO 21
<211> LENGTH: 11
<212> TYPE: PRT
<213> ORGANISM: Artificial Sequence
<220> FEATURE:
<223> OTHER INFORMATION: peptide

```
<400> SEQUENCE: 21

Val Arg Tyr Gly Gly Tyr Tyr Val Phe Asp Tyr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: peptide

<400> SEQUENCE: 22

Lys Ser Val Ser Thr Ser Gly Tyr Ser Tyr
1               5                   10

<210> SEQ ID NO 23
<211> LENGTH: 3
<212> TYPE: PRT
<213> ORGANISM: Artificial Sequence
<220> FEATURE:
<223> OTHER INFORMATION: peptide

<400> SEQUENCE: 23

Leu Val Ser
1

<210> SEQ ID NO 24
<211> LENGTH: 9
<212> TYPE: PRT
<213> ORGANISM: Artificial Sequence
<220> FEATURE:
<223> OTHER INFORMATION: peptide

<400> SEQUENCE: 24

Gln His Ile Arg Glu Leu Thr Arg Arg
1               5

<210> SEQ ID NO 25
<211> LENGTH: 111
<212> TYPE: PRT
<213> ORGANISM: Artificial Sequence
<220> FEATURE:
<223> OTHER INFORMATION: antibody

<400> SEQUENCE: 25

Val Pro Glu Leu Val Ser Phe Ile Ser Leu Ser Leu Thr Cys Thr Val
1               5                   10                  15

Thr Gly Tyr Ser Ile Thr Ser Asp Tyr Ala Trp Asn Trp Ile Arg Gln
            20                  25                  30

Phe Pro Gly Asn Lys Leu Glu Trp Met Gly Tyr Ile Ser Tyr Ser Gly
        35                  40                  45

Ser Thr Ser Tyr Asn Pro Ser Leu Lys Ser Arg Ile Ser Ile Thr Arg
    50                  55                  60

Asp Thr Ser Lys Asn Gln Phe Phe Leu Gln Leu Asn Ser Val Thr Thr
65                  70                  75                  80

Glu Asp Thr Ala Thr Tyr Tyr Cys Ala Arg Ser Leu Leu Pro Asn Trp
                85                  90                  95

Tyr Phe Asp Val Trp Gly Ala Gly Thr Thr Val Thr Val Ser Ser
                100                 105                 110

<210> SEQ ID NO 26
<211> LENGTH: 108
<212> TYPE: PRT
```

```
<213> ORGANISM: Artificial Sequence
<220> FEATURE:
<223> OTHER INFORMATION: antibody

<400> SEQUENCE: 26

Asp Ile Val Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
                20                  25                  30

Gly Tyr Ser Tyr Met His Trp Asn Gln Gln Lys Pro Gly Gln Pro Pro
            35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Gly Gly Pro Ser Trp Lys
            100                 105

<210> SEQ ID NO 27
<211> LENGTH: 8
<212> TYPE: PRT
<213> ORGANISM: Artificial Sequence
<220> FEATURE:
<223> OTHER INFORMATION: peptide

<400> SEQUENCE: 27

Gly Tyr Ser Ile Thr Ser Asp Tyr
1               5

<210> SEQ ID NO 28
<211> LENGTH: 7
<212> TYPE: PRT
<213> ORGANISM: Artificial Sequence
<220> FEATURE:
<223> OTHER INFORMATION: peptide

<400> SEQUENCE: 28

Ile Ser Tyr Ser Gly Ser Thr
1               5

<210> SEQ ID NO 29
<211> LENGTH: 11
<212> TYPE: PRT
<213> ORGANISM: Artificial Sequence
<220> FEATURE:
<223> OTHER INFORMATION: peptide

<400> SEQUENCE: 29

Ala Arg Ser Leu Leu Pro Asn Trp Tyr Phe Asp
1               5                   10

<210> SEQ ID NO 30
<211> LENGTH: 10
<212> TYPE: PRT
<213> ORGANISM: Artificial Sequence
<220> FEATURE:
<223> OTHER INFORMATION: peptide

<400> SEQUENCE: 30

Lys Ser Val Ser Thr Ser Gly Tyr Ser Tyr
1               5                   10
```

<210> SEQ ID NO 31
<211> LENGTH: 3
<212> TYPE: PRT
<213> ORGANISM: Artificial Sequence
<220> FEATURE:
<223> OTHER INFORMATION: peptide

<400> SEQUENCE: 31

Leu Val Ser
1

<210> SEQ ID NO 32
<211> LENGTH: 9
<212> TYPE: PRT
<213> ORGANISM: Artificial Sequence
<220> FEATURE:
<223> OTHER INFORMATION: peptide

<400> SEQUENCE: 32

Gln His Ile Arg Glu Leu Thr Arg Ser
1               5

<210> SEQ ID NO 33
<211> LENGTH: 131
<212> TYPE: DNA
<213> ORGANISM: Artificial Sequence
<220> FEATURE:
<223> OTHER INFORMATION: primer

<400> SEQUENCE: 33
acgtgtacca ccatgggaga aaaaaaaga gaaaaaagat cagtgtggga cgtgtaccac    60
catggtagta aaaaaagag aaaaaagatc catggtagta aaaaaagat caaaaagatc   120 agtggcactc g                                                      131

<210> SEQ ID NO 34
<211> LENGTH: 35
<212> TYPE: DNA
<213> ORGANISM: Artificial Sequence
<220> FEATURE:
<223> OTHER INFORMATION: primer

<400> SEQUENCE: 34
agaacataga agagaatcaa catcagtggc actcg                             35

<210> SEQ ID NO 35
<211> LENGTH: 121
<212> TYPE: DNA
<213> ORGANISM: Artificial Sequence
<220> FEATURE:
<223> OTHER INFORMATION: primer

<400> SEQUENCE: 35
agggaaaagt cttctgtttc aacagagga tggcgtgaac cagcagacaa gagaaagggg    60
acagtcttct gtttccaaca gcatagcttg tgcaggcgcc gcccatttaa ccacacgtaa   120
c                                                                 121

<210> SEQ ID NO 36
<211> LENGTH: 39
<212> TYPE: DNA
<213> ORGANISM: Artificial Sequence
<220> FEATURE:
<223> OTHER INFORMATION: primer

<400> SEQUENCE: 36

```
tccatggtag acagaggagg gggaaatgga tgtggacta                    39
```

<210> SEQ ID NO 37
<211> LENGTH: 36
<212> TYPE: DNA
<213> ORGANISM: Artificial Sequence
<220> FEATURE:
<223> OTHER INFORMATION: primer
<400> SEQUENCE: 37

```
gacagaggat ggggaaaagg atgtggacta tttgga                      36
```

<210> SEQ ID NO 38
<211> LENGTH: 41
<212> TYPE: DNA
<213> ORGANISM: Artificial Sequence
<220> FEATURE:
<223> OTHER INFORMATION: primer
<400> SEQUENCE: 38

```
agacagagga tgggaaatc aatgtggact atttggaaag g                 41
```

<210> SEQ ID NO 39
<211> LENGTH: 45
<212> TYPE: DNA
<213> ORGANISM: Artificial Sequence
<220> FEATURE:
<223> OTHER INFORMATION: primer
<400> SEQUENCE: 39

```
tctatgtgca caggaaagtt tgaagttgtg aaggaaatag cagaa            45
```

<210> SEQ ID NO 40
<211> LENGTH: 40
<212> TYPE: DNA
<213> ORGANISM: Artificial Sequence
<220> FEATURE:
<223> OTHER INFORMATION: primer
<400> SEQUENCE: 40

```
acaggaaagt ttaaagttgt ggaggaaata gcagaaacac                  40
```

<210> SEQ ID NO 41
<211> LENGTH: 46
<212> TYPE: DNA
<213> ORGANISM: Artificial Sequence
<220> FEATURE:
<223> OTHER INFORMATION: primer
<400> SEQUENCE: 41

```
caggaaagtt taaagttgtg aagcgaatag cagaaacaca acatgg           46
```

<210> SEQ ID NO 42
<211> LENGTH: 45
<212> TYPE: DNA
<213> ORGANISM: Artificial Sequence
<220> FEATURE:
<223> OTHER INFORMATION: primer
<400> SEQUENCE: 42

```
aaagttgtga aggaaatagc acgaacacaa catggaacaa tagtt            45
```

<210> SEQ ID NO 43
<211> LENGTH: 43
<212> TYPE: DNA

```
<213> ORGANISM: Artificial Sequence
<220> FEATURE:
<223> OTHER INFORMATION: primer

<400> SEQUENCE: 43
ttgtgaagga aatagcagaa caccaacatg gaacaatagt tat                    43

<210> SEQ ID NO 44
<211> LENGTH: 45
<212> TYPE: DNA
<213> ORGANISM: Artificial Sequence
<220> FEATURE:
<223> OTHER INFORMATION: primer

<400> SEQUENCE: 44
gtgaaggaaa tagcagaaac accacatgga acaatagtta tcaga                 45

<210> SEQ ID NO 45
<211> LENGTH: 45
<212> TYPE: DNA
<213> ORGANISM: Artificial Sequence
<220> FEATURE:
<223> OTHER INFORMATION: primer

<400> SEQUENCE: 45
aaggaaatag cagaaacaca agaaggaaca atagttatca gagtg                 45

<210> SEQ ID NO 46
<211> LENGTH: 40
<212> TYPE: DNA
<213> ORGANISM: Artificial Sequence
<220> FEATURE:
<223> OTHER INFORMATION: primer

<400> SEQUENCE: 46
gacagaaaaa gatagccggg tcaacataga agcagaacct                       40

<210> SEQ ID NO 47
<211> LENGTH: 38
<212> TYPE: DNA
<213> ORGANISM: Artificial Sequence
<220> FEATURE:
<223> OTHER INFORMATION: primer

<400> SEQUENCE: 47
ggacaactga agctcaacgg gtttaagaaa ggaagcac                         38

<210> SEQ ID NO 48
<211> LENGTH: 40
<212> TYPE: DNA
<213> ORGANISM: Artificial Sequence
<220> FEATURE:
<223> OTHER INFORMATION: primer

<400> SEQUENCE: 48
acaactgaag ctcaactggg ctaagaaagg aagcacgctg                       40

<210> SEQ ID NO 49
<211> LENGTH: 10
<212> TYPE: PRT
<213> ORGANISM: Artificial Sequence
<220> FEATURE:
<223> OTHER INFORMATION: pr-M junction
<220> FEATURE:
<221> NAME/KEY: MUTAGEN
<222> LOCATION: (2)..(2)
<223> OTHER INFORMATION: X is K or R
```

```
<220> FEATURE:
<221> NAME/KEY: MUTAGEN
<222> LOCATION: (3)..(3)
<223> OTHER INFORMATION: X is S or A

<400> SEQUENCE: 49

Arg Xaa Xaa Arg Lys Lys Val Val Met Thr
1               5                   10
```

US 11,046,754 B2

DENGUE VIRUS-LIKE PARTICLE, ANTIBODY AGAINST DENGUE VIRUS, AND COMPOSITION COMPRISING THE SAME

CROSS REFERENCE TO RELATED APPLICATIONS

This application is the National Phase of PCT International Application No. PCT/CN2017/107743, filed on Oct. 26, 2017, which claims priority under 35 U.S.C. 119(e) to U.S. Provisional Application No. 62/413,597, filed on Oct. 27, 2016, all of which are hereby expressly incorporated by reference into the present application.

TECHNICAL FIELD

The present invention is related to treatment of Dengue fever, especially to antibody and composition for this purpose as well as method for preparing the same.

DESCRIPTION OF RELATED ART

Dengue virus (DENV), a member of the family Flaviviridae, is a mosquito-borne pathogen with four distinct serotypes including DENV-1 to DENV-4 (1). Currently, it is estimated that DENV infects about 390 million cases globally each year, resulting in 96 million cases clinically apparent from mild fever to dengue hemorrhagic fever (DHF) or the life-threatening dengue shock syndrome (DSS) (2). Although the yellow fever tetravalent dengue vaccine (YFTD) recently got approved by few countries, the lower vaccine efficacy and the limited usage of this vaccine upon population aged more than 9 years old with previous exposure of dengue infection urges the development of second generation of dengue vaccine (3, 4).

SUMMARY

One of the objectives of the present invention is to provide a virus-like particle of dengue virus. Said virus-like particle is used to produce antiserum or antibody that is capable of neutralizing at least two serotypes of dengue virus.

Another of the objectives of the present invention is to provide an antibody that is capable of neutralizing at least one, at least two, at least three or four serotypes of dengue virus.

In order to achieve the aforesaid objectives, the present invention provides an expression vector, encoding a virus-like particle having a membrane protein; wherein said membrane protein comprises a pr-M junction of SEQ ID NO: 49 at its pre-cleaved form.

The present invention also provides a virus-like particle, comprising a membrane protein; wherein said membrane protein comprises a pr-M junction of SEQ ID NO: 49 at its pre-cleaved form.

The present invention more provides a composition, comprising the aforesaid virus-like particle and a pharmaceutically acceptable carrier or a pharmaceutically acceptable adjuvant.

The present invention further provides an isolated anti-dengue virus antibody or an antigen-binding portion thereof comprising: at least one of a heavy chain complementarity determining region 1 (H-CDR1) comprising GYTFTEYT (SEQ ID NO: 19), at least one of a heavy chain complementarity determining region 2 (H-CDR2) comprising INPNNGGTT (SEQ ID NO: 20), at least one of a heavy chain complementarity determining region 3 (H-CDR3) comprising VRYGGYYVFDY (SEQ ID NO: 21), at least one of a light chain complementarity determining region 1 (L-CDR1) comprising KSVSTSGYSY (SEQ ID NO: 22), at least one of a light chain complementarity determining region 2 (L-CDR2) comprising LVS (SEQ ID NO: 23), and at least one of a light chain complementarity determining region 3 (L-CDR3) comprising QHIRELTRR (SEQ ID NO: 24).

The present invention further provides an isolated anti-dengue virus antibody or an antigen-binding portion thereof comprising: at least one of a heavy chain complementarity determining region 1 (H-CDR1) comprising GYSITSDY (SEQ ID NO: 27), at least one of a heavy chain complementarity determining region 2 (H-CDR2) comprising ISYSGST (SEQ ID NO: 28), at least one of a heavy chain complementarity determining region 3 (H-CDR3) comprising ARSLLPNWYFD (SEQ ID NO: 29), at least one of a light chain complementarity determining region 1 (L-CDR1) comprising KSVSTSGYSY (SEQ ID NO: 30), at least one of a light chain complementarity determining region 2 (L-CDR2) comprising LVS (SEQ ID NO: 31), and at least one of a light chain complementarity determining region 3 (L-CDR3) comprising QHIRELTRS (SEQ ID NO: 32).

The present invention also provides a composition comprising the aforesaid isolated anti-dengue virus antibody or an antigen-binding portion thereof and a pharmaceutically acceptable carrier.

The present invention more provides a method for producing an antiserum, comprising: administering an animal with the aforesaid virus-like particle and collecting serum of said animal.

The present invention then provides an antiserum, which is produced by the aforesaid method; wherein said antiserum is capable of neutralizing at least two serotypes of dengue virus of 50% FRµNT titers at a dilution ratio of 1:60; wherein said more than two serotypes are selected from dengue virus type 1, dengue virus type 2, dengue virus type 3, and dengue virus type 4.

The present invention more provides a method for producing an antibody, comprising: administering an animal with the aforesaid virus-like particle; and isolating an antibody from said animal.

The present invention then provides an antibody, which is produced by the method of claim 31; wherein said antibody is capable of neutralizing dengue virus type 1, dengue virus type 2, dengue virus type 3, and dengue virus type 4 of 50% FRµNT titers at 0.24 to 0.58 µg/mL.

DETAILED DESCRIPTION OF THE INVENTION

Figure 1:
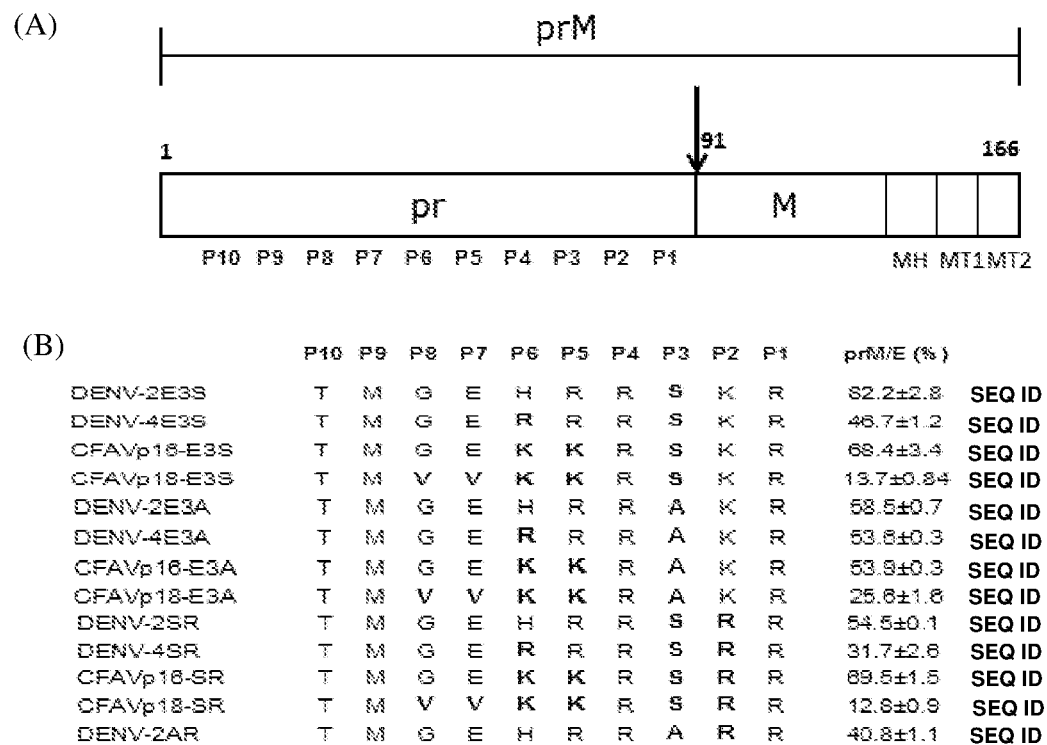
FIG. 1 shows the comparison of pr-M junction cleavage efficiency among different VLPs. (A) Schematic drawing of the prM protein; P1 to P10 is referred as pr-M junction. (B) ELISA results by calculating the percent of prM cleavage. The data are presented as the means+standard deviation (SD) from three representative ELISA experiments with two replicates.

Envelope (E) protein, exposed at the surface of infectious mature virion particles, is the sole target of neutralizing antibodies. During virus replication, newly synthesized immature DENV is assembled in the endoplasmic reticulum at neutral pH, and the pr portion of pre-membrane (prM) protein (See FIG. 1(A)), functioning as a mechanical barrier, positioned to cover the fusion loop (FL) peptide located at the distal end of each E protein of the trimer from early fusion (5, 6). To become fully infectious, the pr portion has to be removed (i.e. be cleaved) by a cellular protease, furin during the egress process. However, the maturation process of DENV is thought to be inefficient and DENV particles are released from infected cells as heterogenous population depending on the degree of cleavage of membrane (M) protein from prM into M protein: immature particles consisting only uncleaved prM protein, partially immature particles containing both prM and M protein and fully mature particles containing only M protein (7, 8). Functional analyses have revealed that complete immature flavivirus lack the ability to infect cells unless under the presence of anti-prM antibodies by the mechanism of antibody-dependent enhancement of infection (ADE) (9, 10). ADE plays an important role of dengue pathogenesis and is modulated by the antibody concentration and the status of virion maturity as shown in West Nile virus (WNV) (11).

Flavivirus virus-like particle (VLP) has been demonstrated as a potential vaccine candidate as its ordered structures are similar to those in the virion envelope and also undergoing low-pH-induced rearrangements and membrane fusion as virion particles (12-14). Thus, we theorized that the process of VLP maturation might be similar to that of DENV virion particles so that VLP might be similarly secreted as heterogeneous population depending on the degree of prM cleavage. To this end, we constructed dengue VLPs with prM amino acid sequences that are either most prone to be cleaved or most resistant to be cleaved, and we characterized these two particles in terms of the antigenicity and structures. As the amino acid sequence is exactly identical except the mutations on furin cleavage site, we hypothesized that the difference in antibody binding or neutralization activity would be highly structure-dependent. In this report we provide evidence that VLPs are ordered as pre-fusion virion structures with the capability to induce cross-reactive neutralizing antibodies.

The term of "E protein" recited hereinafter is referred to the envelop protein of virus or the virus-like particle thereof. In some particular paragraphs, said "E protein" means the envelop protein of Dengue virus or the virus-like particle thereof.

The term of "M protein" recited hereinafter is referred to the membrane protein of virus or the virus-like particle thereof. In some particular paragraphs, said "M protein" means the membrane protein of Dengue virus or the virus-like particle thereof.

The term of "prM protein" or "pr-M protein" recited hereinafter is referred to the pre-membrane protein of virus or the virus-like particle thereof. In other words, the prM protein is referred to the M protein at its pre-cleaved form. In some particular paragraphs, said "prM protein" or "pr-M protein" means the pre-membrane protein of Dengue virus or the virus-like particle thereof.

The term of "pre-cleaved form" is referred to describe a status of the aforesaid M protein at which the pr portion has not been cleaved so that the pr portion remains. Specifically, for instance, as mentioned above, the pr portion is cleaved during the egress process. Thus, before the pr portion is cleaved during the egress process, the M protein is at its pre-cleaved form.

The term of "pr-M junction" or "prM junction" recited hereinafter is referred to a region or peptide of the prM protein where a cellular protease recognizes and cuts at to remove the pr portion of a prM protein and make it into a mature M protein. The term "pr portion" is a segment of polypeptide of a prM protein that is to be removed, cut, or cleaved during the egress process. Specifically, the "pr-M junction" is referred to the P1 to P10 indicated in FIG. 1(A).

The term of "prM/E ratio" recited hereinafter is referred to the ratio of the amount of prM protein and the amount of E protein of a population of virus-like particles at issue. Preferably, said prM/E ratio can be determined by ELISA or Western blotting by the methods disclosed in the specification.

The term of "M/E ratio" recited hereinafter is referred to the ratio of the amount of M protein and the amount of E protein of a population of virus-like particles at issue. Preferably, said M/E ratio can be determined by ELISA or Western blotting by the methods disclosed in the specification. Alternatively, said M/E ratio can be calculated from the prM/E ratio determined to the same population of virus-like particles at issue, for instance, by the following formula: 1−(prM/E ratio).

The term of "50% FRµNT titers" is referred to the meaning that is well-known in the field while conducting a Focus-reduction microneutralization test (i.e. FRµNT). The description of "capable of neutralizing . . . at a dilution ratio of 1:60" or alike is referred to describe the neutralization can be achieved at a dilution ratio of 1:60 or lower dilution ratio thereof, such as 1:50, 1:40, 1:30, 1:20, 1:10, 1:5 or 1:1. Likewise, "capable of neutralizing . . . at a dilution ratio of 1:100" or alike is referred to describe the neutralization can be achieved at a dilution ratio of 1:100 or lower dilution ratio thereof, such as 1:90, 1:80, 1:70, 1:60, 1:50, 1:40, 1:30, 1:20, 1:10, 1:5 or 1:1; "capable of neutralizing . . . at a dilution ratio of 1:70" or alike is referred to describe the neutralization can be achieved at a dilution ratio of 1:70 or lower dilution ratio thereof, such as 1:60, 1:50, 1:40, 1:30, 1:20, 1:10, 1:5 or 1:1. The description of "capable of neutralizing . . . at 0.24 to 0.58 µg/mL" or alike is referred to describe the neutralization can be achieved at the indicated concentration in a FRµNT test.

One aspect of the present invention is to provide a virus-like particle, an expression vector encoding the same and a composition comprising the same. Said virus-like particle comprises a membrane protein having a pr-M junction of SEQ ID NO: 49 at its pre-cleaved form. In a preferable embodiment, said pr-M junction comprises SEQ ID NO: 5, SEQ ID NO: 9, or SEQ ID NO: 13. In another preferable embodiment, said expression vector comprises SEQ ID NO: 16.

Usually a virus-like particle contains more than one membrane protein and more than one pr portion at its pre-cleaved form. In a preferable embodiment, the virus-like particle of the present invention is able to undergo almost cleavage of the pr portions thereof. In an alternative embodiment, said almost cleavage is referred to a cleavage efficiency of at least 70%. In a preferable embodiment, the cleavage efficiency of the pr portion is at least 70%, 80% or 90%. In a more preferable embodiment, the cleavage efficiency of the pr portion is 100%.

In an alternative embodiment, said composition comprising the virus-like particle of the present invention might further comprise a pharmaceutically acceptable carrier or a pharmaceutically acceptable adjuvant. Said composition can be used to produce antiserum or antibody, which is capable of neutralizing dengue virus in a subject. In a preferable embodiment, said composition can be used for inducing cross-reactive neutralizing antibodies in an object. In a preferable embodiment, said composition can be used for dengue fever prevention.

As used herein, the term "pharmaceutically acceptable carrier" is intended to include any and all solvents, dispersion media, coatings, antibacterial and antifungal agents, isotonic and absorption delaying agents and the like, which is compatible with pharmaceutical administration. For instance, said pharmaceutically acceptable carrier might include but not limited to water, mannitol, lactose, starch, magnesium stearate, or combination thereof.

As used herein, the term "pharmaceutically acceptable adjuvant" is intended to include any and all reagent that is capable to enhance the immune response induced by an active ingredient (ex. the virus-like particle of the present invention). For instance said pharmaceutically acceptable adjuvant might include but not limited to an aluminum adjuvant or an oil-in-water type suspension adjuvant containing squalene (AS03, MF59, or the like), ligands of Toll-like receptor such as CpG and 3-O-desacyl-4'-monophosphoryl lipid A (MPL), a saponin-based adjuvant, a polymer-based adjuvant such as poly-γ-glutamic acid, and polysaccharides such as chitosan and inulin.

Another aspect of the present invention is about a method for producing antiserum or antibody, antiserum or antibody produced by said method, and compositions comprising the same.

The method for producing an antiserum comprises administering an animal with said virus-like particle of the present invention; and collecting serum of said animal. In an alternative embodiment, said administering can be achieved by intramuscular injection. In a preferable embodiment, said virus-like particle is formulated as a composition before use. In a more preferable embodiment, said virus-like particle is formulated as said composition of the present invention having a pharmaceutically acceptable carrier or a pharmaceutically acceptable adjuvant. In an alternative embodiment, said collecting can be achieved by any means that is well-known and well-practiced in the field.

In an alternative embodiment, said antiserum is evaluated by enzyme-linked immunosorbent assay (ELISA) or FRμNT. In a preferable embodiment, said antiserum is capable of neutralizing at least two serotypes of dengue virus of 50% FRμNT titers at a dilution ratio of 1:60; wherein said more than two serotypes are selected from dengue virus type 1, dengue virus type 2, dengue virus type 3, and dengue virus type 4.

In another preferable embodiment, said antiserum is capable of neutralizing at least two serotypes of dengue virus of 50% FRμNT titers at a dilution ratio of 1:100; wherein said more than two serotypes are selected from dengue virus type 1, dengue virus type 2, dengue virus type 3, and dengue virus type 4. In another preferable embodiment, said antiserum is capable of neutralizing dengue virus type 1, dengue virus type 2, and dengue virus type 4 of 50% FRμNT titers at a dilution ratio of 1:70. In a more preferable embodiment, said antiserum is capable of neutralizing dengue virus type 1, dengue virus type 2, dengue virus type 3, and dengue virus type 4 of 50% FRμNT titers at a dilution ratio of 1:60.

The method for producing an antibody comprises administering an animal with the virus-like particle of the present invention; and isolating an antibody from said animal. In an alternative embodiment, said antibody is isolated from blood or spleen of said animal. In an alternative embodiment, the splencytes of said animal are harvested and fused with myeloma cells. In a preferable embodiment, said antibody is capable of neutralizing dengue virus type 1, dengue virus type 2, dengue virus type 3, and dengue virus type 4 of 50% FRμNT titers at 0.24 to 0.58 μg/mL.

In an alternative embodiment, said administering can be achieved by intramuscular injection. In a preferable embodiment, said virus-like particle is formulated as a composition before use. In a more preferable embodiment, said virus-like particle is formulated as said composition of the present invention having a pharmaceutically acceptable carrier or a pharmaceutically acceptable adjuvant. In an alternative embodiment, said isolating can be achieved by any means that is well-known and well-practiced in the field.

In a preferable embodiment, the present invention provides an isolated anti-dengue virus antibody or an antigen-binding portion thereof comprising: at least one of a heavy chain complementarity determining region 1 (H-CDR1) comprising GYTFTEYT (SEQ ID NO: 19), at least one of a heavy chain complementarity determining region 2 (H-CDR2) comprising INPNNGGTT (SEQ ID NO: 20), at least one of a heavy chain complementarity determining region 3 (H-CDR3) comprising VRYGGYYVFDY (SEQ ID NO: 21), at least one of a light chain complementarity determining region 1 (L-CDR1) comprising KSVSTSGYSY (SEQ ID NO: 22), at least one of a light chain complementarity determining region 2 (L-CDR2) comprising LVS (SEQ ID NO: 23), and at least one of a light chain complementarity determining region 3 (L-CDR3) comprising QHIRELTRR (SEQ ID NO: 24). In a preferable embodiment, said isolated anti-dengue virus antibody or an antigen-binding portion thereof comprises at least one of a heavy chain comprising SEQ ID NO: 17 and at least one of a light chain comprising SEQ ID NO: 18. In another preferable embodiment, said anti-dengue virus antibody or an antigen-binding portion thereof is able to bind to Domain 2 of E protein of a dengue virus. In another preferable embodiment, said anti-dengue virus antibody or an antigen-binding portion thereof is able to bind to W101 of said Domain 2. The term "W101" is referred to the 101st amino acid of said Domain 2, which is a Tryptophan.

In a preferable embodiment, the present invention provides an isolated anti-dengue virus antibody or an antigen-binding portion thereof comprising: at least one of a heavy chain complementarity determining region 1 (H-CDR1) comprising GYSITSDY (SEQ ID NO: 27), at least one of a heavy chain complementarity determining region 2 (H-CDR2) comprising ISYSGST (SEQ ID NO: 28), at least one of a heavy chain complementarity determining region 3 (H-CDR3) comprising ARSLLPNWYFD (SEQ ID NO: 29), at least one of a light chain complementarity determining region 1 (L-CDR1) comprising KSVSTSGYSY (SEQ ID NO: 30), at least one of a light chain complementarity determining region 2 (L-CDR2) comprising LVS (SEQ ID NO: 31), and at least one of a light chain complementarity determining region 3 (L-CDR3) comprising QHIRELTRS (SEQ ID NO: 32). In a preferable embodiment, said isolated anti-dengue virus antibody or an antigen-binding portion thereof comprises at least one of a heavy chain comprising SEQ ID NO: 25 and at least one of a light chain comprising SEQ ID NO: 26. In another preferable embodiment, said anti-dengue virus antibody or an antigen-binding portion thereof is able to bind to Domain 3 of E protein of a dengue virus. In another preferable embodiment, said anti-dengue virus antibody or an antigen-binding portion thereof is able to bind to E311 of said Domain 3. The term "E311" is referred to the 311st amino acid of said Domain 3, which is a Glutamic acid.

The present invention also provides a composition comprising an effective amount of the aforesaid antibody or antiserum. The composition might further comprise a pharmaceutically acceptable carrier. Said pharmaceutically acceptable carrier is defined as set forth in the preceding paragraphs. Said "effective amount" is an amount sufficient to neutralize dengue virus under the conditions of administration.

The following examples recite the trials and experiments of the present invention in order to further explain the features and advantages of the present invention. It shall be noted that the following examples are exemplary and shall not be used for limiting the claim scope of the present Experiment 1: Cleavage Prediction and Determination of prM/E Ratio by ELISA and Western Blotting The C-terminal of prM protein contains an α-helical domain (MH) in the stem region, followed by two transmembrane domains (MT1 and MT2). Please see FIG. 1A, the down-arrow indicated the prM cleavage site. Numbers refer to the position of the amino acids in the polyprotein starting with the first amino acid of prM according to DENV-2 (GenBank accession number: NP 056776; RKERRHEGMTTCTG; SEQ ID NO: 01).

In order to determine the cleavage efficiency of the prM protein of a DENV-2 virus-like particles (VLP), 13 VLPs with different pr-M junctions was constructed based on the pr-M junction of DENV-2 (GenBank accession number: NP_056776; RKERRHEGMTTCTG; SEQ ID NO: 01). ELISA assay was conducted to determine the prM/E ratio of the VLPs having the aforesaid pr-M junction. The lower the prM/E ratio, the higher the cleavage efficiency.

The result of the prM/E ratio determined by ELISA was labeled in FIG. 1(B). According to the result, CFAVp18-

E3S, CFAVp18-E3A, and CFAVp18-SR were ranked the top three highest cleavage efficiency among the VLPs.

Figure 2:
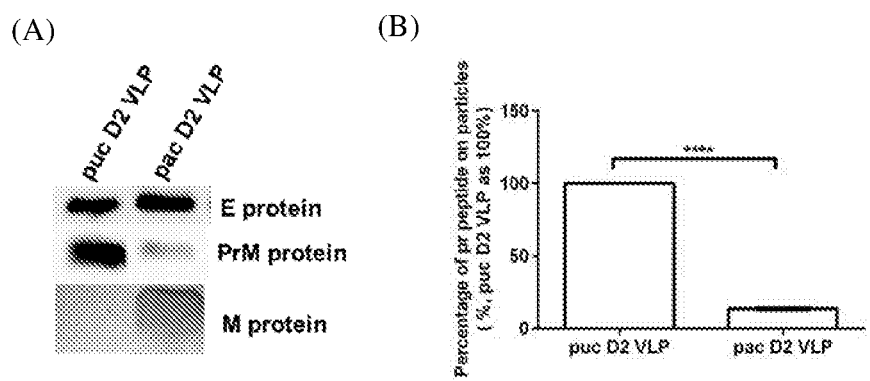
FIG. 2 shows (A) Result of the Western blotting of the culture supernatants of pucD2VLPs and pacD2VLPs after electroporation of the respective plasmids. The reduction of prM protein of pacD2VLP was due to the increase the cleavage of pr peptide as significant banding of the M protein was observed. No M protein was observed for pucD2VLP due to the resistance to furin cleavage by mutation on the furin recognition sequences. (B) ELISA results to measure the relative quantity of E and prM protein by using MAb3H5 (specific for DENV-2 domain III) and 155-49 (specific for DENV prM). Percent cleavage of prM was then calculated with reference to prM-uncleaved VLP, which was referred to pucD2VLP and assumed to be 100% uncleaved. The data are presented as the means±standard deviation (SD) from three representative ELISA experiments with two replicates.

To further confirm the cleavage of prM, DENV-2 VLP were harvested from transfected tissue culture fluid and further purified for Western blotting. The results were consistent with that from ELISA (FIG. 1B) that the prM-almost-cleaved VLP (pacD2VLP; indicated as CFAVp18-E3S in FIG. 1B) retained only about 10% of pr peptide on the surface of the particles, compared to the prM-uncleaved VLP (pucD2VLP having pr-M junction (P1-P10) of TSER-RHEGMT; SEQ ID NO: 15), whose prM was assumed to be 100% uncleaved (FIG. 2A and Table 1).

A further ELISA was conducted by using MAb 3H5 (specific for DENV-2 domain III) and 155-49 (specific for DENV prM) to show relative quantity of E and prM protein of pacD2VLP and pucD2VLP. The result confirmed the extremely high cleavage efficiency of pacD2VLP in comparison with pucD2VLP.

TABLE 1

|  | E | PrM | M | PrM/E ratio |
| --- | --- | --- | --- | --- |
| puc D2 VLP | 100 | 100 | 0 | 100 |
| pac D2 VLP | 123.76 | 10.72 | 100 | 8.7 |

Set E and prM of puc D2 VLP as 100
Set M of pac D2 VLP as 100

In light of the foregoing, four plasmids (See SEQ ID NO: 16 for the whole sequences of the plasmid of pacD2VLP) expressing the four VLP samples of the present invention were selected for subsequent experiments. The four sample plasmids of the present invention having amino acid sequences of the pr-M junction thereof as shown in the following Table 2.

TABLE 2

| Sample No. | Pr-M junction (P1~P10)* | SEQ ID NO. |
| --- | --- | --- |
| Sample 1 (pacD2VLP) | RKSRKKVVMT | SEQ ID NO: 05 |
| Sample 2 | RKARKKVVMT | SEQ ID NO: 09 |
| Sample 3 | RRSRKKVVMT | SEQ ID NO: 13 |
| Sample 4 (pucD2VLP) | TSERRHEGMT | SEQ ID NO: 15 |
| Wild type | RKERRHEGMT | SEQ ID NO: 01 |

*Numbers refer to the positions of the amino acid relative to the pr-M cleavage site in the proximal direction.

Experiment 2: Immunogenicity of the VLPs of the Present Invention

To define the influence of prM cleavage level on the immunogenicity of D2VLP, we immunized groups of 4-week old BALB/c mice at weeks 0 and 4 with 4 µg VLP per mice. The D2VLPs (Sample 1 and Sample 4) used in this experience were concentrated and purified from clarified supernatants.

Figure 3:
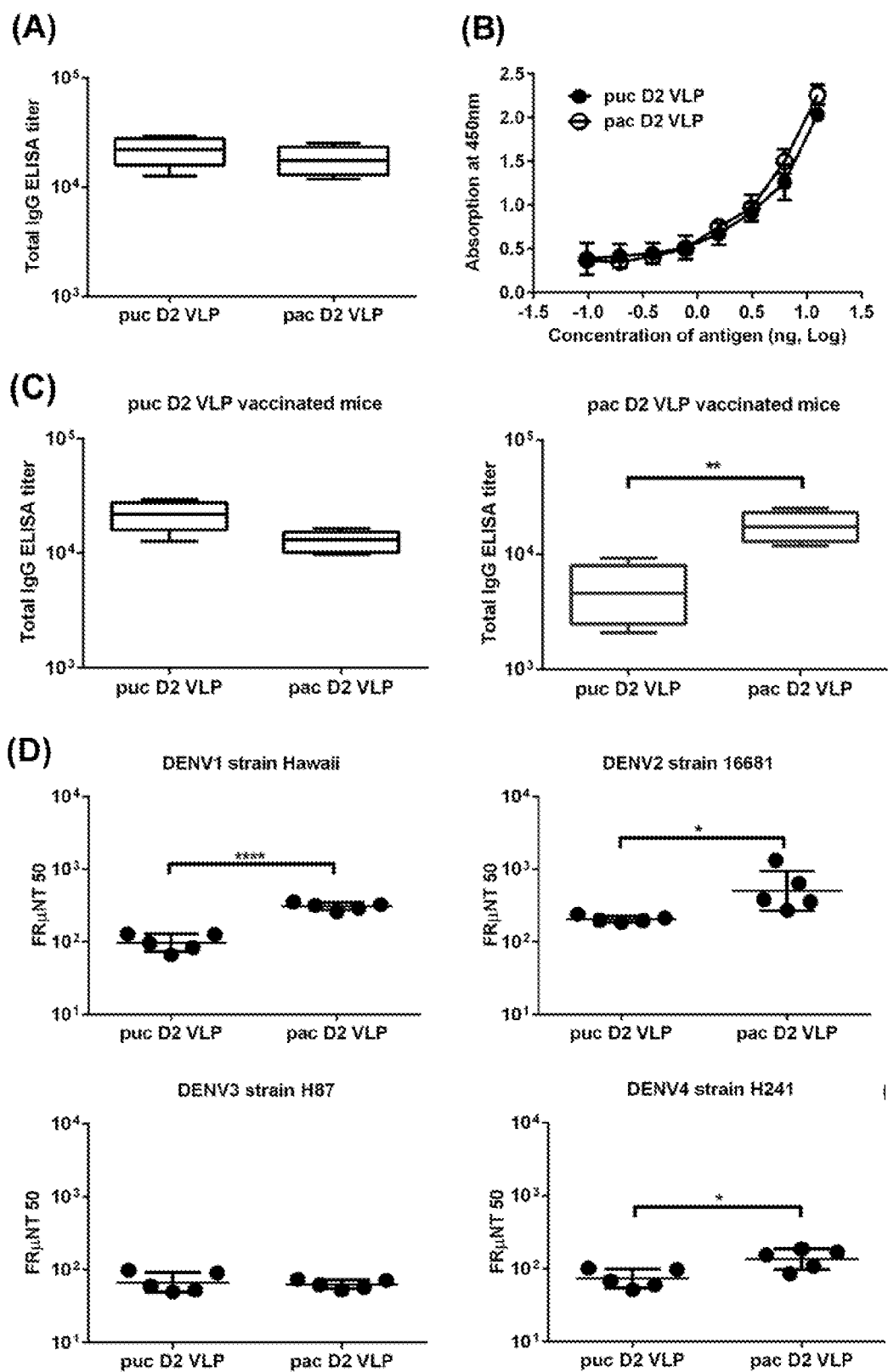
FIG. 3 shows the total antigen-specific IgG, neutralizing titers and proportion of anti-prM antibodies between two groups of mice immunized with pucD2VLP or pacD2VLP with all pr-peptide uncleaved or nearly all pr-peptide cleaved on particle surface, respectively. 4 weeks mice were immunized (i.m.) with 4 ug of D2VLP at 0 and 4 weeks. (A) showed the endpoint IgG titer 12 weeks post-immunization of two different groups of mice on homologous antigens. (B) Standard curve of D2VLPs used in these experiments. (C) showed the endpoint IgG titer 12 weeks post-immunization of mice sera receiving pucD2VLP or pacD2VLP using both homologous and heterologous D2VLP antigens. Equal amounts of both antigens were used here based on the standard curves generated using the purified VLPs. Geometric means and 95% confidence intervals are depicted unless otherwise noted. All endpoint titers were log 10 transformed and statistical significance was determined using the Mann-Whitney U test to account for non-normality of some transformed data. (D) showed the 50% antigen focus-reduction micro neutralization titers (FRμNT50) for all serotypes of DENV. A student's t test was utilized here as both data sets were normally distributed. (E) Proportions of anti-prM antibodies from two different D2VLP immunization groups were further confirmed using epitope-blocking ELISA. Percent blocking of an HRP-labeled anti-prM Mab (2H2) by sera from mice vaccinated different D2VLP to pucD2VLP was determined by the formula 100*[(OD450pucD2VLP-OD450pucD2VLP blocked by 2H2)/OD450pucD2VLP] at 1000-fold dilution of mice sera. (F) Serial dilutions of pucD2VLP and mutant pucD2VLP (puc Δ2H2) containing mutations in the Mab 2H2 binding epitope (K26P, K21D, F1A) were tested the binding by Mab 2H2 (left) and control antibody 3H5 (right) by binding-ELISA. (G) The bar graph displaying results from an antigen-capture ELISA shows that comparable amounts of WT and mutant VLPs were added based on the recognition of E by Mab 3H5 (Left). Serial dilutions of the serum from mice immunized with pucD2VLP (middle) and pacD2VLP (right) were subjected to a binding-ELISA using wild-type and mutant pucD2VLP. (H) Proportions of anti-prM antibodies from two different D2VLP immunization groups were calculated based on the formula 100*[(OD450pucD2VLP-OD450pucΔ2H2)/OD450pucD2VLP] at 1000-fold dilution of mice sera (left). *, $p<0.05$. , $p<0.01$. *, $p<0.001$, ****, $p<0.0001$.
Figure 3:
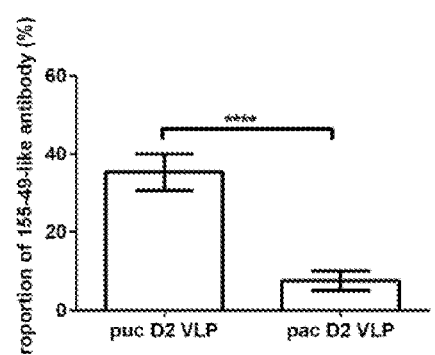
Figure 3:
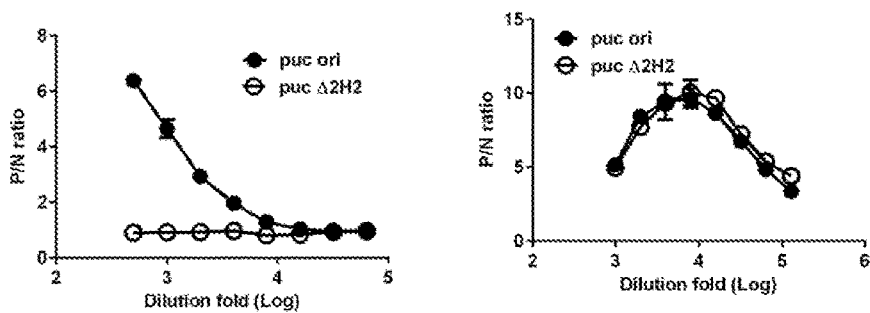
Figure 3:
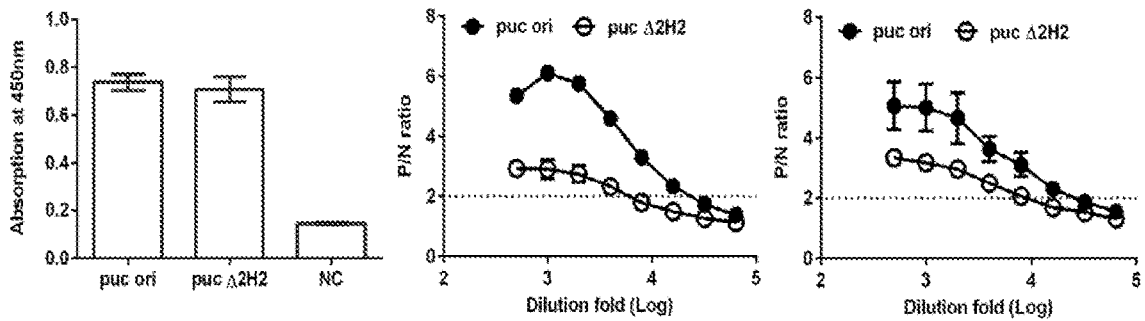
Figure 3:
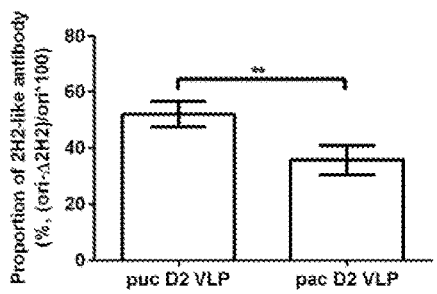

At 4 and 8 weeks after the second immunization, blood samples were collected and individual serum was analyzed for an antibody response by ELISA. The total protein concentration of purified pucD2VLP and pacD2VLP were first determined by the Bradford assay and then subjected to antigen-capture ELISA after 2-fold serial dilution. All the mice immunized with pucD2VLP (Sample 4) and pacD2VLP (Sample 1) induced significantly high anti-DENV-2-specific antibodies against homologous antigens with no statistical differences (FIG. 3A). In order to precisely quantify the amount of dengue-specific antibodies, purified VLPs under individual preparations were used as standards by antigen-capture ELISA (FIG. 3B). The IgG response from the 8-week post-vaccinated sera in mice vaccinated with pacD2VLP showed significantly greater titers (1:15346) against the homologous pacD2VLP antigen than the heterologous pucD2VLP antigens (1:6381) (FIG. 3C, middle and right).

To rigorously analyze the influence of the prM cleavage level on the immunogenicity of D2VLP, a FRµNT against four serotypes of DENV was conducted using individual mouse serum. The serum of the mice receiving pacD2VLP immunization induced higher neutralization titers against all serotypes of DENV (50% of FRµNT for DENV-1: 331, DENV-2: 597 and DENV-4: 141) than the pucD2VLP vaccinated group (50% of FRµNT for DENV-1: 100, DENV-2: 207 and DENV-4: 76), except DENV-3 with 1:70 and 1:64 of 50% FRµNT titers for the pucD2VLP and pacD2VLP vaccinated groups, respectively (FIG. 3D).

Without being bound by theory or any existing hypothesis, we suggested that the higher neutralization activity induced by pacD2VLP was partly due to the reduction of anti-prM antibodies. To compare the proportion of anti-prM antibodies in vaccinated mice sera between different immunization groups, we first used epitope-blocking ELISA and compared the percentage of anti-prM antibodies blocked by anti-prM monoclonal antibody (MAb 2H2) in vaccinated mice sera receiving pucD2VLP or pacD2VLP. The results showed that only 7.59% of 155-49-like antibodies in sera of pacD2VLP immunized mice, compared to 35.26% in pucD2VLP vaccinated groups (FIG. 3E).

Moreover, to avoid steric hindrance of MAb binding, we further generated a mutant pucD2VLP by mutating three amino acids (K26P+K21D+F1A) (FIG. 3F). Next, the sera from the immunized mice were tested their binding to the wild-type and mutant pucD2VLP. The results also suggested that significant lower proportion of 2H2-like antibodies (35.68%) were induced by pacD2VLP immunized mice, compared to 52.12% in pucD2VLP vaccinated groups (FIG. 3G and FIG. 3H).

Experiment 3: Purification of Antibody Generated by pacD2VLP of the Present Invention We performed fusion and generated hybridoma from the splenocytes of the pacD2VLP vaccinated mouse. Among all 72 hybridomas screened, the two selected MAbs were sequenced and named as DM25-3 and DM8-6 respectively. According the sequencing results, DM25-3 has a heavy chain of:

(SEQ ID NO: 17)
GEPGTSLKISCKTSGYTFTEYTMYWVKQSHGKSLEWIGGINPNNGGTTYN

QKFKGKATLTVNKSSSIAYMEVRNLTSEDSAVYYCVRYGGYYVFDYWGQG

TTLTVSS

-continued and the complementarity determining regions thereof are (SEQ ID NO: 19)
GYTFTEYT, (SEQ ID NO: 20)
INPNNGGTT,
and (SEQ ID NO: 21)
VRYGGYYVFDY;
and a light chain of:
(SEQ ID NO: 18)
TLWKTQSPASLAVSLGQRATISYRASKSVSTSGYSYMHWNQQKPGQPPRL

LIYLVSNLESGVPARFSGSGSGTDFTLNIHPVEEEDAATYYCQHIRELTR

RRGPSSR and the complementarity determining regions thereof are (SEQ ID NO: 22)
KSVSTSGYSY, (SEQ ID NO: 23)
LVS,
and (SEQ ID NO: 24)
QHIRELTRR.

According the sequencing results, DM8-6 has a heavy chain of:
(SEQ ID NO: 25)
VPELVSFISLSLTCTVTGYSITSDYAWNWIRQFPGNKLEWMGYISYSGST

SYNPSLKSRISITRDTSKNQFFLQLNSVTTEDTATYYCARSLLPNWYFDV

WGAGTTVTVSS and the complementarity determining regions thereof are (SEQ ID NO: 27)
GYSITSDY, (SEQ ID NO: 28)
ISYSGST,
and (SEQ ID NO: 29)
ARSLLPNWYFD;
and a light chain of:
(SEQ ID NO: 26)
DIVMTQSPASLAVSLGQRATISYRASKSVSTSGYSYMEIWNQQKPGQPPR

LLIYLVSNLESGVPARFSGSGSGTDFTLNIHPVEEEDAATYYCQHIRELT

RSEGGPSWK and the complementarity determining regions thereof are (SEQ ID NO: 30)
KSVSTSGYSY, (SEQ ID NO: 31)
LVS,
and (SEQ ID NO: 32)
QHIRELTRS.

Figure 4:
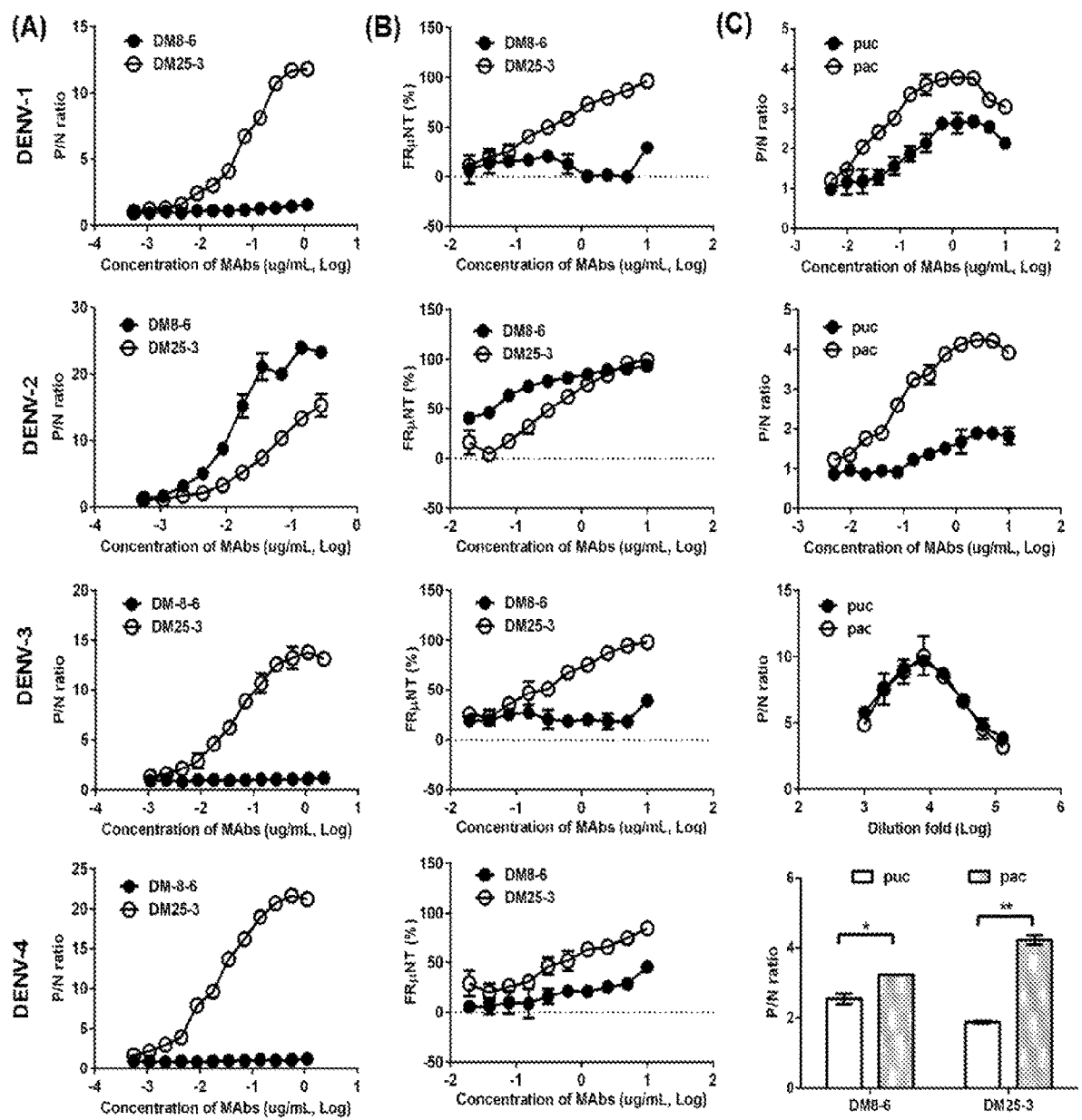
FIG. 4 shows the characterization of murine monoclonal antibodies generated from the splenocytes of pacD2VLP immunized mouse. (A) Binding activity of DM8-6 and 25-3 against DENV-1 to 4 were measured using binding ELISA. (B) Neutralizing activity of DM8-6 and 25-3 against DENV-1 to 4 were measured using focus-reduction microneutralization test (FRμNT). (C) Binding-ELISA of DM8-6 (Top), DM25-3 (second to the top) and MHIAF (third to the top) against pucD2VLP and pacD2VLP were performed. The antigens were used at a single standardized concentration producing an optical density (OD) of 0.8, which was chosen as it standardized all three antigens to be equal quantity based on the standard curves by antigen-capture ELISA. The largest difference in binding activity of both MAbs was converted to bar chart (Bottom). (D) Binding-ELISA against pucD2VLP and pacD2VLP was performed using mice sera immunized with two doses of pucD2VLP (left) or pacD2VLP (center). The difference in binding activity of both MAbs was converted to bar chart at 1:1000 fold dilution of mice sera (Right). (E) Equal amounts of pacD2VLP and mutant pucD2VLP containing mutations at amino acid residue 101 (W101G) and 311 (E311R) were tested the binding by DENV-2 mouse hyper-immune ascetic fluid (MHIAF) (left), DM 25-3 (middle) and DM8-6 (right) by binding-ELISA. While MHIAF showed equal binding to all three VLPs, DM25-3 lost binding to W101G mutant VLP and DM8-6 showed significant loss of binding activity to E311R. The data are presented as the means±standard deviation (SD) from three representative ELISA experiments with two replicates. *, $p<0.05$. **, $p<0.01$. (F) DENV-specific B-cell repertoires from the splenocytes obtained from both pacD2VLP and pucD2VLP immunized mice. B-cell producing heavy chains and light chains encoded by the same IgH and IgL gene loci were grouped by the same color. The proportions of all IgH or IgL genes, with k-chain are indicated by colors if the frequency in the B-cell population of each vaccinated group is greater than 10%. Otherwise it will be shown in white.
Figure 4:
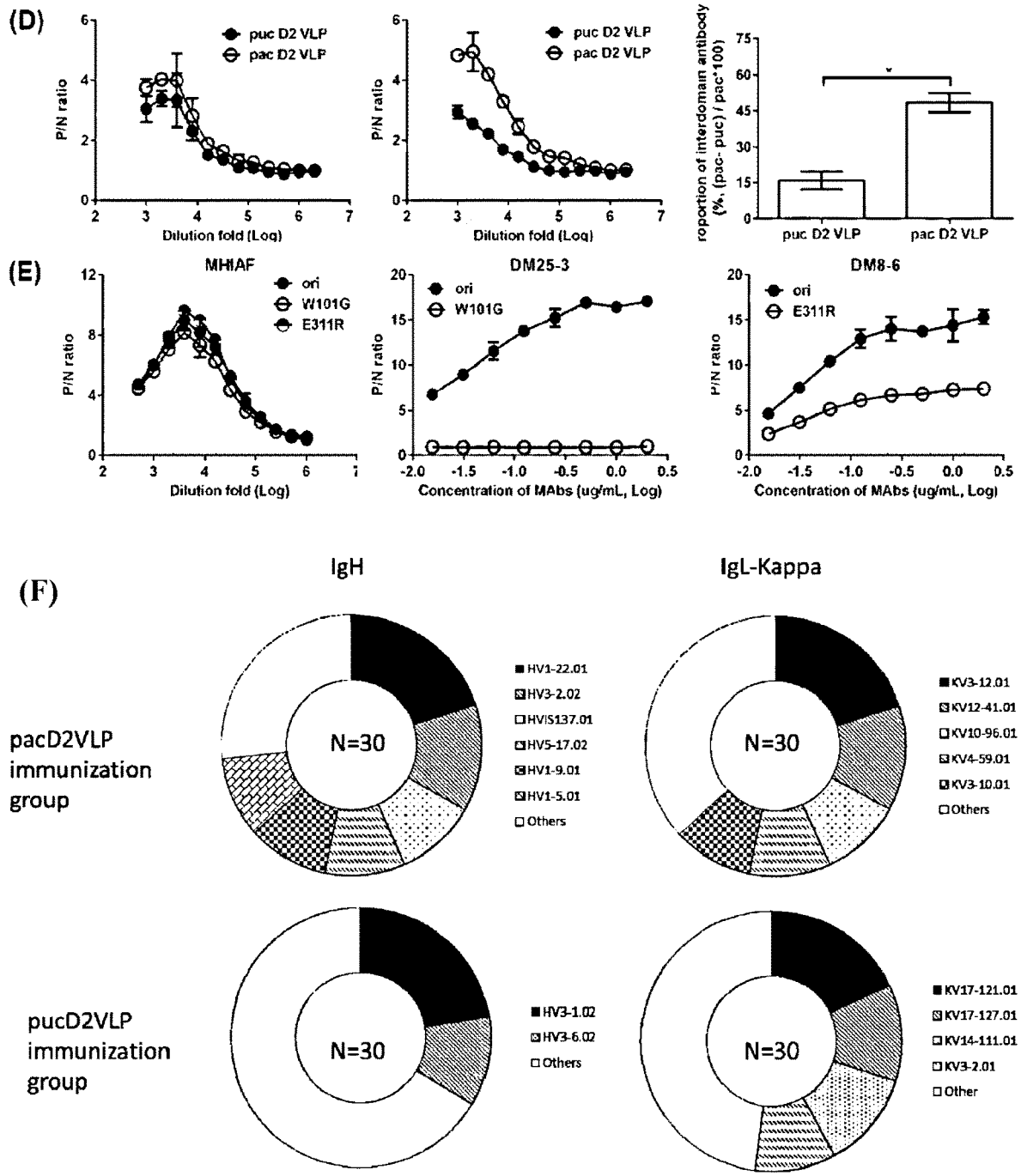

The reactivities of two selected MAbs to all four serotypes of DENV were evaluated by using binding-ELISA shown in FIG. 4A. The results showed that DM8-6 is a serotype-specific MAb and on the contrary, DM25-3 recognized all four serotypes of DENV. Next, we tested the neutralizing activity of these two MAbs against all four serotypes of DENV. DM8-6 showed good neutralizing activity against DENV-2 at a concentration of 0.037 μg/mL for 50% FRμNT but poorly neutralize the other serotypes. Consistent with the binding-ELISA results, DM25-3 neutralized all four serotypes at concentration of 0.32, 0.38, 0.24, 0.58 μg/mL for DENV-1 to DENV-4, respectively (FIG. 4B). Interestingly, DM25-3 recognized pacD2VLP well, but poorly recognized pucD2VLP (FIG. 4C). Comparing the binding of the post-immunized mice sera on both pacD2VLP and pucD2VLP, significant different binding curves were observed in pacD2VLP immunized mice, which converted to 48.5% of DM25-3-like antibodies (FIG. 4D). However, little differences in the binding curves on both pacD2VLP and pucD2VLP antigens were observed, which converted to 16% of DM25-3-like antibodies in pucD2VLP immunized mice, respectively.

Experiment 4: Identification of the Epitope of DM25-3 and DM8-6

Figure 5:
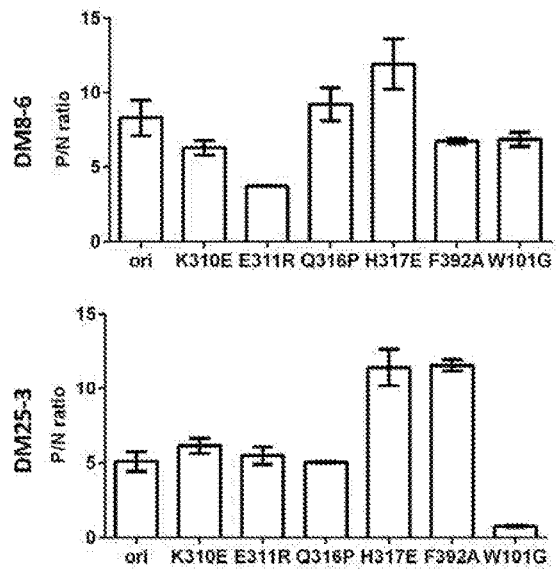
FIG. 5 shows the identification of neutralizing epitopes of MAb 25-3 and 8-6. Bar graph displays decreases in MAb reactivities in binding-ELISA for pacD2VLPs with substitutions at the listed residues. Various DENV-2 virus-like particle (VLP) mutants were expressed in COS-1 cells by electroporating various plasmid DNAs. Tissue-culture media were harvested 3 days after transfection and clarified for antigen-capture ELISA. (Top) Substitutions of E311R led to a significantly reduced binding activity of neutralizing MAb DM8-6, compared to wild-type D2VLP designated as ori. (Bottom) Substitutions of W101G led to a completely loss of binding by MAb DM25-3, compared to ori. Data shown are one representative experiment out of three independent experiments.

In order to identify the epitope of DM25-3, site-directed mutagenesis was performed. Instead of performing shot-gun random mutagenesis, we focused on the fusion loop peptide on domain II and A-strand on domain III, which has been suggested to be the important binding regions for cross-reactive group/complex neutralizing antibodies. For this purposes, mutant plasmids, respectively including substitutions at K310E, E311R, Q316P, H317E, F392A, and W101G, indicated can be secreted outside the cells were used for further epitope mapping by binding ELISA. The results showed that DM25-3 recognized residue 101 on the fusion loop peptide of domain II ((FIG. 5, FIG. 4E). On the contrary, mutations on domain III affect DM8-6 binding, particularly residue 311 on AB loop.

The completeness of mutant VLPs including W101G, K310E and E311R were further confirmed by using a panel of DENV-2 MAbs, including group-cross-reactive antibodies (4G2, 4A1B-9, 6B3B-3, 6B6C-1, DM25-3, T5-1, DM8-6) recognizing all four major pathogenic flavivirus serocomplexes; complex cross-reactive antibodies (T5-1) recognizing all four DENV complex viruses, and type-specific antibody (DM8-6) recognizing DENV-2 only. The relative binding of MAbs was determined by dividing the OD450 of mutant D2VLPs by that of original pacD2VLP (Table 3).

TABLE 3

| Relative binding (%) | W101G | K310E | E311R |
|---|---|---|---|
| 4G2 | 9 ± 0.7 | 109.6 ± 5.2 | 99.4 ± 7.5 |
| 4A1B-9 | 46.3 ± 8.2 | 84.3 ± 12.2 | 83.9 ± 4.7 |
| 6B3B-3 | 12.1 ± 0.1 | 111.9 ± 5.7 | 82.8 ± 8.2 |
| 6B6C-1 | 40.6 ± 3 | 127.1 ± 19.8 | 101 ± 18.9 |
| DM25-3 | 5.6 ± 0.3 | 128.6 ± 6.6 | 98.4 ± 5.9 |
| T5-1 | 93.4 ± 11.2 | 12.5 ± 2.1 | 30.9 ± 2.7 |
| DM8-6 | 119.5 ± 1.8 | 89.2 ± 2 | 41.7 ± 0.5 |

Set pac D2 VLP as 100% and calculate following: mutant/ori * 100

To further confirm if DM25-3 quaternary structure-dependent epitopes of whole virion particles, a recombinant DENV-2 was produced by replacing domain III with consensus domain III (PL046cEDIII) and the results of binding-ELISA from both parental DENV-2 strain PL046 and PL046cEDIII was compared. Consistent with the results from epitope mapping, significant loss of binding to DENV-2 of DM8-6 was observed when domain III was removed. Surprisingly, the loss of binding to PL046cEDIII of DM25-3 was also noticed (FIG. 6A), which suggested that fusion-loop-recognizing DM25-3 is an E inter-domain dimer antibody. Further comparing the 50% FRµNT of the post-immunized mice sera on both PL046 and PL046cEDIII, 89.1% of inter-domain antibodies were observed in the sera of the pacD2VLP immunized mice, compared to 51.1% in the pucD2VLP mice, with statistical significance (FIG. 6B).

Figure 7:
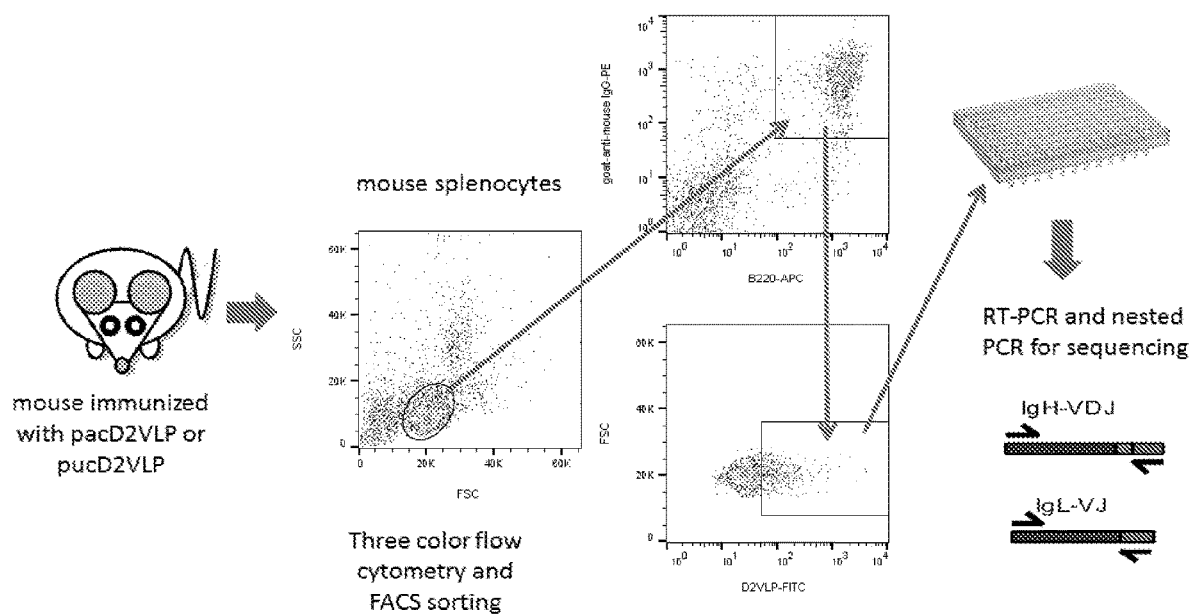
FIG. 7 shows the overview of experimental design. Single DENV(+), B220(+) and IgG1(+)-specific B cells from the spleen of vaccinated mice were sorted into 96-well plates by FACS. The IgH and IgL gene transcripts of each single B cell were amplified by RT-PCR and nested PCR by gene-specific primers as previous described (T. Tiller et al., *J Immunol Methods* 350, 183 (2009)).

To better understand the B-cell repertoires after immunization with pacD2VLP and pucD2VLP, the splenic B cells capable of binding to DENV-2 virion from the spleens of pacD2VLP or pucD2VLP-vaccinated mice were sorted into ten 96-well plates with only single cell per well (FIG. 7). By analyzing the amino acid sequences of the RT-PCR products of the variable regions of Ig heavy-chain (IgH) and Ig light-chain (IgL) genes from two groups, the B-cell response from pacD2VLP-immunized group was more complex than those from the pucD2VLP group, particularly the gene loci of IgH (FIG. 4F). The IgH and IgL genes from DM25-3 were also analyzed and found containing IgHV1-22*01 and IgKV3-12*01, which were clonally expanded as shown in FIG. 4F.

Experiment 5: Structure Analysis of VLP of the Present Invention

Figure 8:
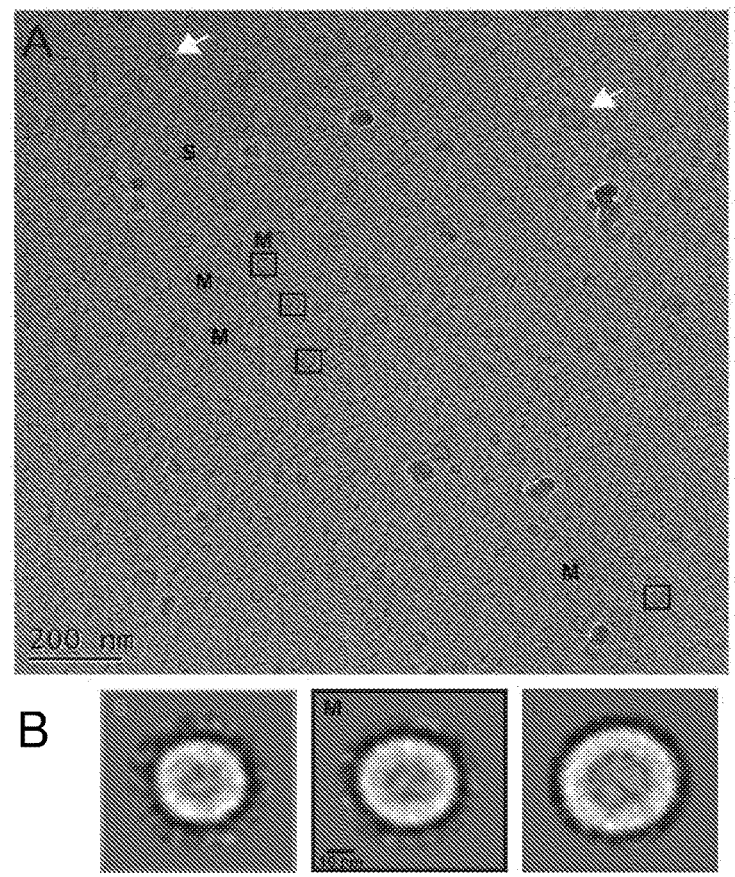
FIG. 8 shows (A) CryoEM images of purified DENV VLPs in mature form showed spherical particles (boxed) among irregular or incomplete ones (arrows). In the population of spherical particles, there were three populations found by classification analyses: smaller particles which was indicate by "S", "medium" particles by "M" and "larger" particles by "L". They were boxed in blue, black and red colors, respectively. We eliminated these irregular particles as much as possible through visual inspection and used the spherical particles for further image analyses. (B) The spherical particles were under 2D classification and averaging, it also showed that the picked spherical particles had size variation. It also showed that the bilayer is not perfectly spherical and the density might be smeared out during data process.
Figure 9:
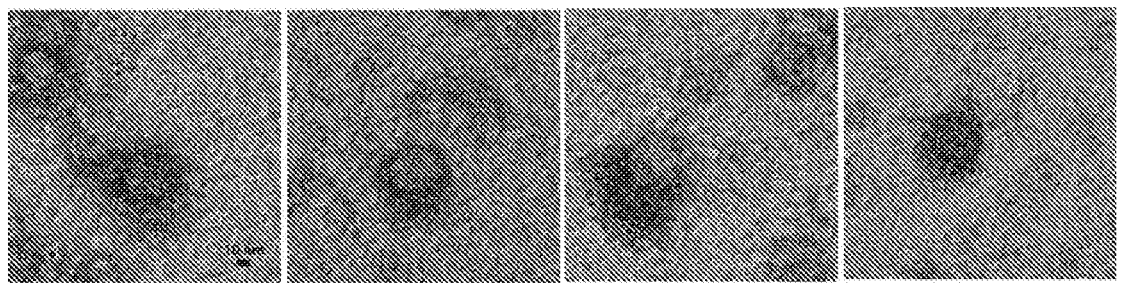
FIG. 9 shows the gallery of the transmission EM images of immunogold-labeled DENV VLPs. The E proteins were labeled with antibody to domain III of E protein conjugated to 6-nm gold particles.

Cryo-EM analysis of DENV VLPs (pacD2VLP) demonstrated that the VLPs had a distribution of variable sizes (FIG. 8 and Table 4). The immunogold labeling detected the VLPs as the particles with a diameter of ~31 nm (FIG. 9), which was also the major peak in the population.

TABLE 4

| | Particle Size | | |
|---|---|---|---|
| | S-27 nm | M-30-32 nm | L-35-37 nm |
| Population (%) | 31 | 43 | 26 |

Figure 10:
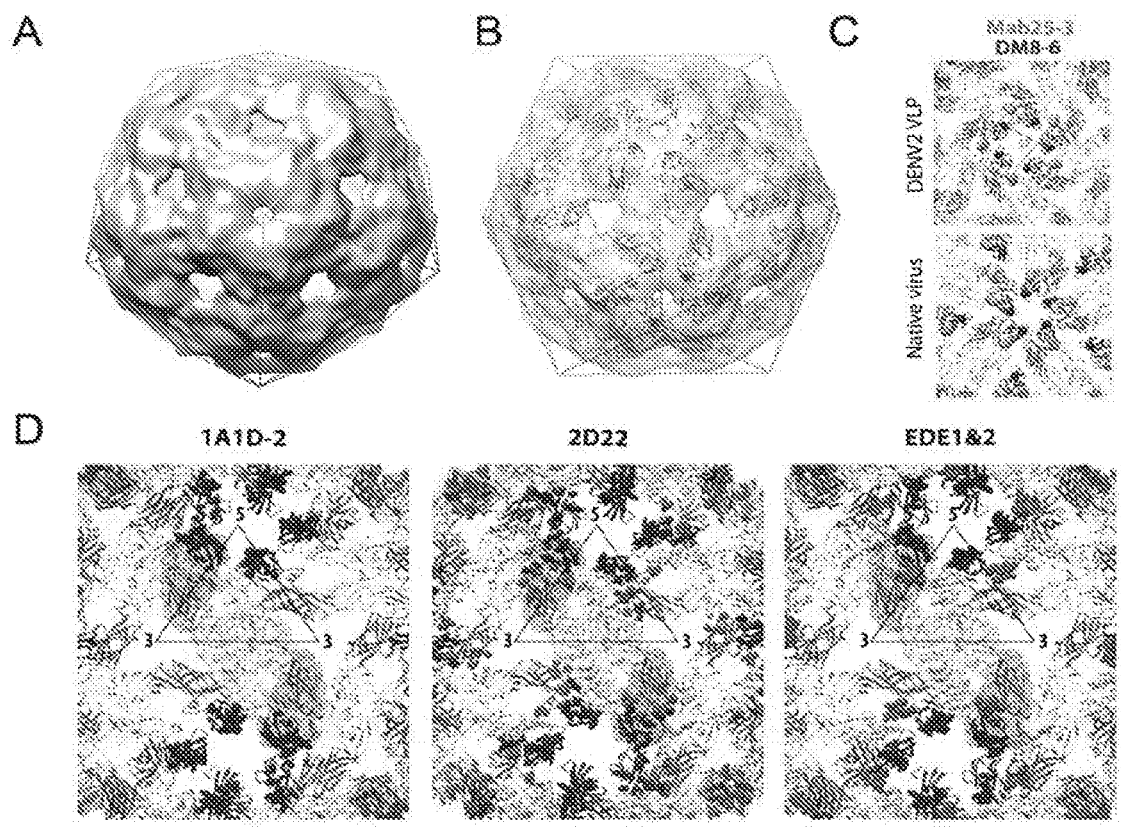
FIG. 10 shows the structure of mature form virus-like particles (pacD2VLP) of dengue virus serotype 2. (A) The reconstructed cryoEM map of the DENV VLPs. Icosahedral 2-, 3- and 5-fold axes were indicated by icosahedral cage. (B) The fitting of sE (PDB: 3J05) protein into cryoEM density map. The density map was shown as a transparent volume rendering into which was fitted the backbone structures of the sE proteins. The domain I, II, III were colored by yellow, red and blue, respectively. It was noteworthy that the E1 structure followed the T=1 icosahedral symmetry lattice with 30E dimer subunits on the surface and the accessibility of antibodies. (C) The fitted sE into VLPs (upper panel) and native virus (lower panel) were viewed from 5-fold axis. The 5-fold opening in native virus was narrower than the one in VLPs which made the restricted monoclonal antibodies (MAb) DM25-3 and DM8-6 antibody accessibility. The antibody recognition sites at amino acids 101 and 311 were shown in orange and blue spheres, which were located at the periphery of the holes near the 5-fold axis of E dimer. The line connected by the spheres showed the distances between amino acids and revealed the possibility of binding of both two fab from the same antibody. The distances were all below 87 Å which was the maximum distance between two Fabs of an IgG. (D) MAb 1A1D-2, 2D22 and EDE1 and 2 are representative antibodies representative of dengue-complex, serotype-specific and flavivirus-group reactive neutralizing antibodies. Previous studies suggested that they bind to quaternary hidden epitopes, which are not exposed on virion particles under 28° C. in neutral pH. Their binding footprint analysis showed that the two Fabs on MAb 1A1D-2, 2D22 and EDE1 and 2 were able to bind all of the E dimers on VLPs without steric crash. Importantly, the binding footprints of all three antibodies are highly overlapping and form a neutralization sensitive patch on VLPs. The residues that interact with antibody were shown as spheres. The black triangle represented the asymmetric unit of the VLP.
Figure 11:
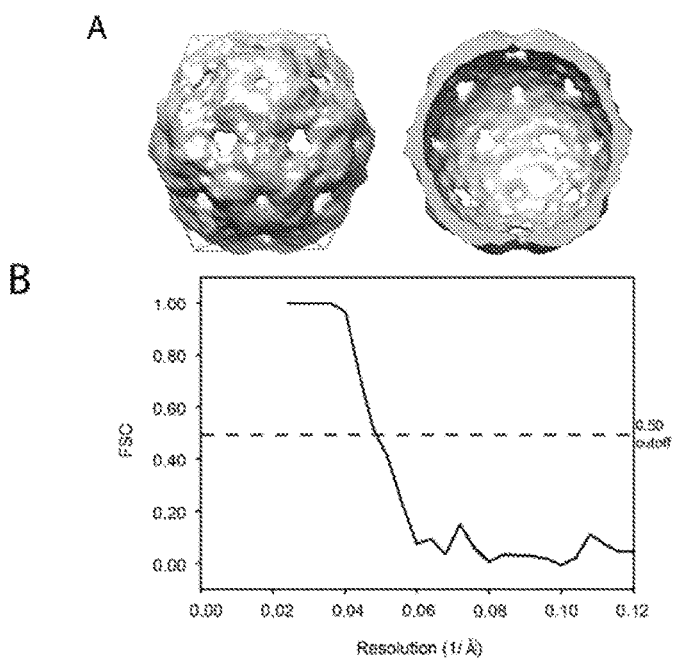
FIG. 11 shows (A) The reconstructed cryoEM map of the DENV VLPs. Icosahedral 2-, 3- and 5-fold axes were indicated by icosahedral cage. On the right, the closest half of the density map had been removed to reveal the hollow structure. (B) Fourier shell correlation (fsc) plots for final maps of the DENV VLP. The resolution of the final reconstruction was determined to be 23 Å using 0.5 fsc cutoff.
Figure 12:
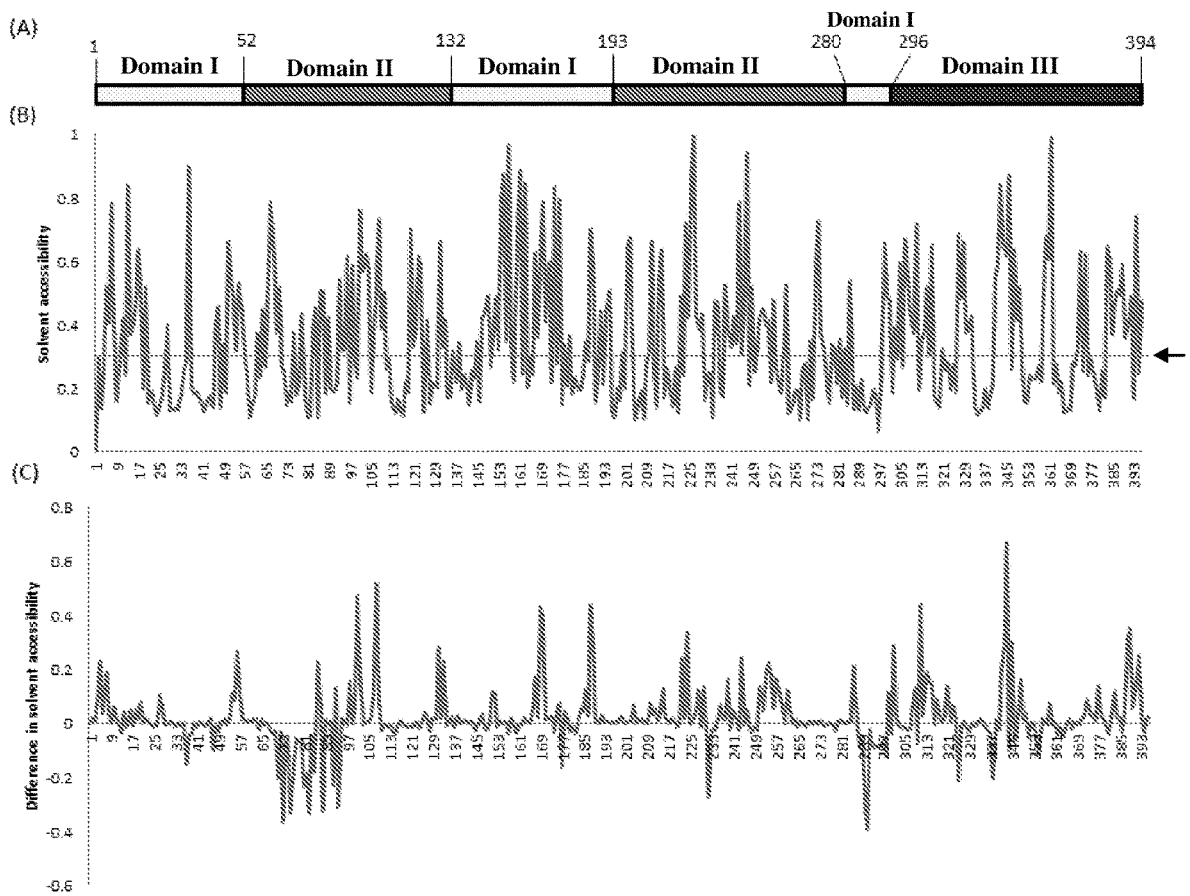
FIG. 12 shows the solvent accessibility of envelope protein ectodomain amino acid residue 1-396 of dengue virus serotype 2 virus-like particles. (A) Domain definition of dengue E. Domain I, II, III were indicated, respectively. (B) Solvent accessible surface area (SASA) of individual amino acid molecule on pacD2VLP was calculated by POPS program. The red line (arrow) indicated the solvent accessibility ≥0.3. (B) The difference of solvent accessibility between VLP and DENV-2 virion particles (PDB: 3J27). The positive value indicated the solvent accessibility of VLP is higher than virion particle and the negative value indicated the opposite direction. The highest positive values are focused in three peptide regions including amino acid residue ranging from 100-110, the fuson loop peptide; from 309-317, the A strand of domain III; from 342-348, the DE loop of domain III.

The cryo-EM and 3D reconstruction approach showed that the VLPs at 23 Å had a hollow structure with smooth surface (FIG. 10 and FIG. 11). Fitting the atomic soluble E protein into the cryoEM density map showed that the VLPs followed the T=1 icosahedral symmetry with 30E dimer subunits on the surface (FIG. 10B), the similar arrangement was also found in TBEV VLPs (14). The apparent features of the VLPs structure comparing to the native particles (6, 25) were the E protein organization at 3-fold axes mimic the fusogenic state of virion particles preparing for fusion (26). The fusogenic state mimicry of VLP exposed more accessible epitopes (48.2%; 191 amino acid with 30% solvent accessibility of 396 entire E protein) compared to virion particle with 177 amino acids (44.7%), particularly located at fusion loop region and AB loop of domain III. (FIG. 12). Consistent with the results from this study, DM25-3, capable of neutralizing all four serotypes of DENV, recognized residue 101 of fusion loop, which was located on the edge of protrusion at the periphery of the holes near the 5-fold axis of E dimer, which can only be exposed when virion particles undergo conformational change under the low pH environment (FIG. 10C).

Figure 13:
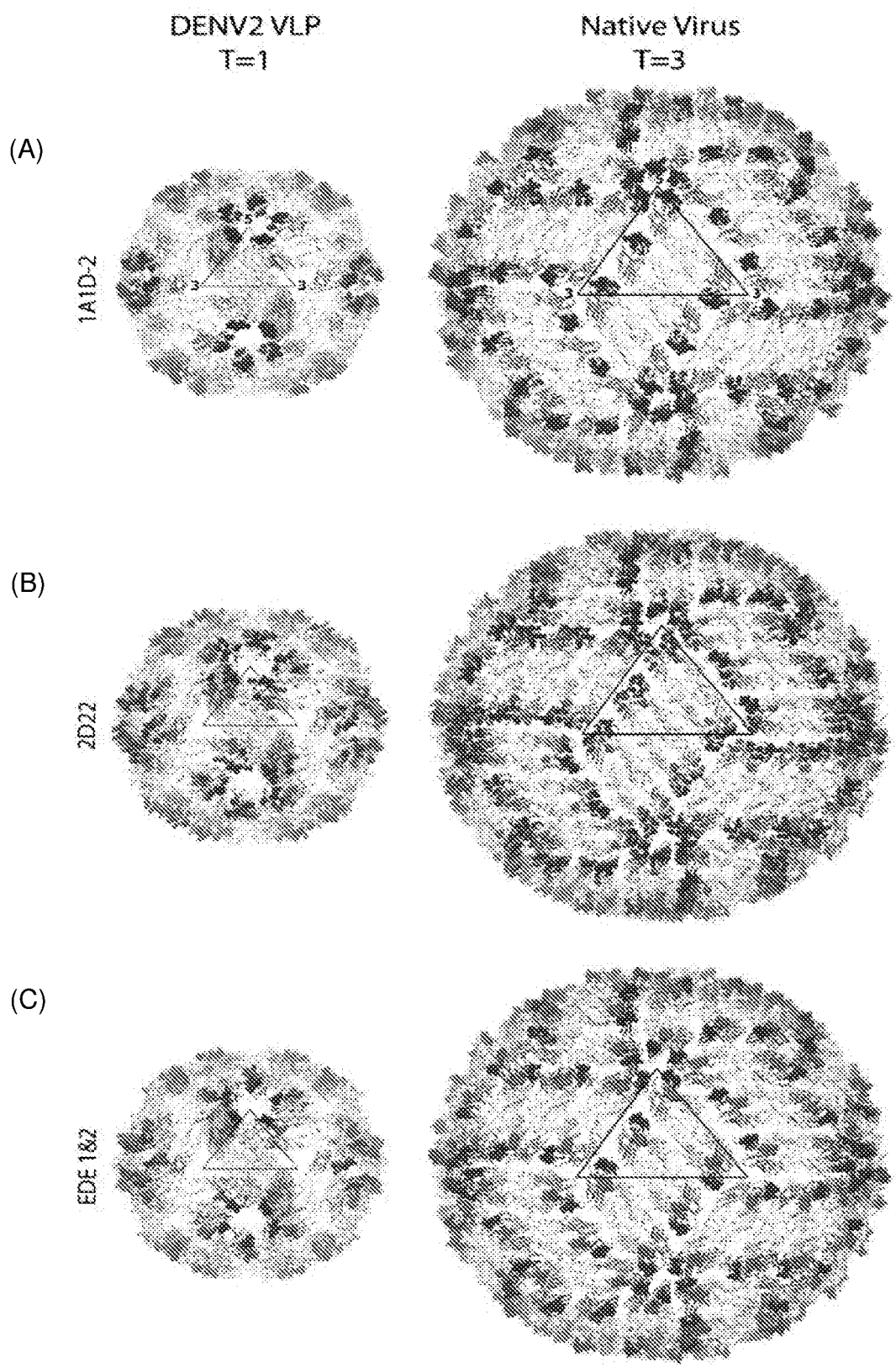
FIG. 13 shows Fabs footprint of antibody 1A1D-2, 2D22 and EDE1 and 2 on VLP and virion particle. Footprint analysis showed that the two Fabs on antibody 1A1D-2, 2D22 and EDE1 &2 were able to bind all of the E dimers on VLPs without steric crash. (A) The Fab fragments of M which binds to the virus at 37° C. (17) were expected to be bind better to VLPs most likely due to the larger holes around 5-fold axes. (B) Human antibody (2D22) could block two-thirds of or all dimers ability on the virus surface, depending on the strain (18), while in the VLPs, 2D22 could block almost all the dimers without steric interference most likely due to the larger openings at 5-fold axes than native virus. (C) The 'E-dimer-dependent epitope', which recognized by broadly neutralizing antibodies EDE1 and 2 (19) were also well exposed in VLPs. The residues that interact with antibody were shown as spheres. The domains were colored as shown previously.

Recent studies suggested that the potent neutralizing human monoclonal antibodies with broadly reactivity across the dengue serocomplex can be induced from dengue patients, particularly after secondary infection (22, 23, 27). Our findings here suggested that pacD2VLP, structurally mimicking their viral fusogenic counterparts, is capable of inducing such cross-reactive antibodies with broad neutralizing activity with predominantly 48% in the mouse-vaccinated sera. The packing of E dimers from VLP, different from virion particles, provides an unique open-space structure with features by increasing epitope accessibility, which are previously thought cryptic in mature virion particles under 28° C. and neutral pH environment. By superimposing those E-dimer dependent quaternary epitopes onto the VLP (23, 28, 29), the binding footprints of those antibodies are highly overlapping and form a "neutralization sensitive site" on VLPs (FIG. 10D, FIG. 13). The mechanisms of pacD2VLP in inducing higher and broader immune response are at least through: (1) epitope accessibility governs the induction of neutralizing antibodies; (2) removal of decoy epitopes presenting on prM-containing structure such as pucD2VLP, which prone to induce antibodies recognizing prM. In summary, as an alternative choice for vaccine candidates, VLP vaccines have the advantages of being highly immunogenic, noninfectious, and accessible to quality control as well as the scaling-up during production. The unique properties of pacD2VLP make them an excellent model system to explore the potential of a universal dengue travel vaccine and the potential to be the second generation of dengue vaccine.

Materials and Methods
Viruses, Cells and Antibodies

The strains of DENV serotype 1-4 used here include Hawaii, 16681, H87 and H241, respectively. COS-1 (ATCC CRL 1650; ATCC) and C6/36 cells were grown in Dulbecco's modified Eagle's medium (DMEM, Gibco, Life Technologies, Grand Island, N.Y.) supplemented with 10% heat-inactivated fetal bovine serum (FBS, Hyclone, ThermoFisher, Mass.), 0.1 mM nonessential amino acids (Gibco, Life Technologies, Grand Island, N.Y.), 7.5% NaHCO3, 100 U/ml penicillin, and 100 ug/ml streptomycin. 5% FBS was used for vero cells. Cells were maintained at 37° C. with 5% CO2, except for C6/36 cells, which were maintained at 28° C. without CO2. Parental DENV-2 strain PL046 generated from infectious clone and the domain III-swapped PL046, with domain III of DENV-2 replaced by consensus sequence as described previously (H. Chen et al., Arch Virol 158, 1523 (2013)), were provided by Dr. Y L Lin from Academia Sinica, Taiwan.

Murine monoclonal antibody (MAb) 2H2 recognizing DENV-2 prM, serotype-specific MAb 3H5-1 antibody recognizing DENV-2 only, rabbit serum and mouse hyperimmune ascitic fluid (MHIAF) for DENV-1 to 4 were provided by one of the authors, G J Chang (DVBD, CDC, Fort Collins, Colo.). A panel of DENV-2 MAbs, including group-cross-reactive antibodies (4G2, 4A1B-9, 6B3B-3, 6B6C-1, DM25-3, T5-1, DM8-6) recognizing all four major pathogenic flavivirus serocomplexes; complex cross-reactive antibodies (T5-1) recognizing all four DENV complex viruses, and type-specific antibody (DM8-6) recognizing DENV-2 only as previously described (reference #20), was also provided by one of the authors, G J Chang. MAb 155-49 recognizing DENV-2 prM was obtained from H Y Lei (National ChengKung University, Taiwan). MAbs 155-49 was also labeled with biotin using EZ-Link™ Sulfo-NHS-Biotin kit (Thermo Fisher Scientific Inc., Rockford, Ill.) according to the manufacturer's instruction. In order to increase the recognition of M protein, anti-M antibody was produced by cloning the complete M protein sequence into pET21a (Novagen, Germany) and purified under the denaturing condition as described in molecular cloning handbook. 10 µg of purified M protein with complete Freud's adjuvant was used to immunize the mice by intraperitoneal route for five times with 2 weeks interval and the final sera were collected. Anti-B220 antibody and IgG were purchased from AbCam.

The previously constructed and characterized recombinant plasmid pVD2i expressing the prM and 80% envelope proteins of DENV-2 Asian 1 genotype, 16681 strain (H. Hughes et al., *Virol J* 9, 115 (2012)), was used in this study and herein termed pVD2. The furin cleavage site of prM was mutated on pVD2 to generate a prM-uncleaved plasmid as shown previously or as indicated in FIG. 1 by using site-directed mutagenesis by following the manufacturer's protocol (Stratagene, La Jolla, Calif.). The primers used for cloning and site-directed mutagenesis were provided in Table 5. All the plasmids were confirmed containing no other mutations other than indicated by sequencing the complete transcripts.

Sequence Analysis of Flavivirus Pr/M Sites

Flavivirus prM protein sequence alignments were performed using ClustalX 2.1 software with the following sequences: dengue virus serotype 2 (NP_056776), dengue virus serotype 1 (AIU47321), dengue virus serotype 3 (YP_001621843), dengue virus serotype 4 (NP_073286), Japanese encephalitis virus (NP_775664), St. Louis encephalitis virus (AIW82235), West Nile virus (AIO10814), tick-borne encephalitis virus (NP_775501), yellow fever virus (NP_041726), cell-fusion agent virus (NP_041725), Zika virus (BAP47441.1). Sequences of pr/M junction region were scored for their predicted cleavability by furin using the PiTou 2.0 software package (2); (www.n-uolan.net/reference.html). A negative score indicates a sequence predicted not to be cleaved by furin, whereas a positive score denotes prediction of furin cleavability.

TABLE 5

| Name | SEQ ID NO. | Primer sequence (5'-3') | Amino acid substitution | Secretion |
|---|---|---|---|---|
| mD2VLP | SEQ ID NO: 33 | ACGTGTACCACCATGGGAGAAAA AAAAAGAGAAAAAAGATCAGTG | His-Lys, Arg-Lys | Y |
| | | TGGGACGTGTACCACCATGGTAG TAAAAAAAAGAGAAAAAAGATC | Gly-Val, Glu-Val | Y |
| | | CATGGTAGTAAAAAAAAGATCAA AAAGATCAGTGGCACTCG | Glu-Ser | Y |
| imD2VLP | SEQ ID NO: 34 | AGAACATAGAAGAGAATCAACAT CAGTGGCACTCG | Lys-Ser, Arg-Thr | Y |
| Δ2H2 | SEQ ID NO: 35 | AGGGAAAAGTCTTCTGTTTCCAA CAGAGGATGGCGTGAAC | Lys-Pro | Y |
| | | CAGCAGACAAGAGAAAGGGGACA GTCTTCTGTTTCCAACAG | Lys-Asp | Y |
| | | CATAGCTTGTGCAGGCGCCGCCC ATTTAACCACACGTAAC | Phe-Ala | Y |
| W101G | SEQ ID NO: 36 | TCCATGGTAGACAGAGGAGGGGG AAATGGATGTGGACTA | Trp-Gly | Y |
| N103K | SEQ ID NO: 37 | GACAGAGGATAGGGGAAAAGGAT GTGGACTATTTGGA | Asn-Lys | N |
| G104Q | SEQ ID NO: 38 | AGACAGAGGATGGGGAAATCAAT GTGGACTATTTGGAAAGG | Gly-Gln | N |
| K307E | SEQ ID NO: 39 | TCTATGTGCACAGGAAAGTTTGA AGTTGTGAAGGAAATAGCAGAA | Lys-Glu | N |
| K310E | SEQ ID NO: 40 | ACAGGAAAGTTTAAAGTTGTGGA GGAAATAGCAGAAACAC | Lys-Glu | Y |
| E311R | SEQ ID NO: 41 | CAGGAAAGTTTAAAGTTGTGAAG CGAATAGCAGAAACACAACATGG | Glu-Arg | Y |
| E314R | SEQ ID NO: 42 | AAAGTTGTGAAGGAAATAGCACG AACACAACATGGAACAATAGTT | Glu-Arg | N |
| T315H | SEQ ID NO: 43 | TTGTGAAGGAAATAGCAGAACAC CAACATGGAACAATAGTTAT | Thr-His | N |
| Q316P | SEQ ID NO: 44 | GTGAAGGAAATAGCAGAAACACC ACATGGAACAATAGTTATCAGA | Gln-Pro | Y |
| H317E | SEQ ID NO: 45 | AAGGAAATAGCAGAAACACAAGA AGGAACAATAGTTATCAGAGTG | His-Glu | Y |
| P364R | SEQ ID NO: 46 | GACAGAAAAAGATAGCCGGGTCA ACATAGAAGCAGAACCT | Pro-Arg | N |
| W391G | SEQ ID NO: 47 | GGACAACTGAAGCTCAACGGGTT TAAGAAAGGAAGCAC | Trp-Gly | N |
| F392A | SEQ ID NO: 48 | ACAACTGAAGCTCAACTGGGCTA AGAAAGGAAGCACGCTG | Phe-Ala | Y |

Antigen Production and VLP Purification

To produce VLP antigens, COS-1 cells at a density of $1.5 \times 10^7$ cells/mL were electroporated with 30 μg of each pVD2 plasmid following the previously described protocol (G. Chang et al., *J Virol* 74, 4244 (2000)). After electroporation, cells were seeded into a 75-cm$^2$ culture flasks (Corning Inc., Corning, N.Y., USA) containing 15 mL growth medium and allowed to recover overnight at 37° C. The growth medium was replaced the next day with a maintenance medium containing serum-free medium (SFM4MegaVir™, SH30587.01, Hyclone, ThermoFisher) supplemented with NEAA, GlutaMAX, sodium pyruvate and cholesterol (Gibco, Life Technologies, Grand Island, N.Y.), and cells were continuously incubated at 28° C. with 5% $CO_2$ for VLP secretion. Tissue-culture media were harvested 3 days after transfection and clarified by centrifugation at 8,000×g for 30 min at 4° C. in AF-5004CA rotor (Kubota, Tokyo, Japan) with Kubota 3740 centrifuge. The harvested media was first concentrated 20-fold by 100K Amicon Ultra centrifugal filters (Merck Millpore, Calif.) before subjecting to 20% sucrose cushion by ultracentrifugation at 28,000 rpm for 16 hours at 4° C. in a Beckman SW28 rotor and resuspended in 250 μl TNE buffer (50 mM Tris-HCl, 100 mM NaCl, 0.1 mM EDTA and pH 7.4) per 1 liter of harvested medium at 4° C. overnight. The VLPs were further purified by rate zonal centrifugation in a 5 to 25% sucrose gradient at 25,000 rpm at 4° C. for 3 hours. All gradients were made with TNE buffer and were centrifuged in a Beckman SW41 rotor. Fractions of 0.5 ml were collected by upward displacement and assayed for antigen-capture ELISA. For experiments in which highly purified material was required, VLPs with the top 6 highest OD from antigen-capture ELISA were pelleted at 40,000 rpm at 4° C. for 4 hours in a Beckman SW41 rotor and re-suspended in 250 μl THE buffer in total. The protein concentration was measured by using Bradford assay (BioRad, Hercules, Calif.) by following the commercial protocol and using bovine serum albumin (BSA, New England Biolabs, Mass.) as standard. Purified VLPs were also labeled with fluorescence for antigen-specific B cell sorting by following the manufacture's protocol (S. Zhang et al., *J Virol Methods* 167, 172 (2010)).

ELISA

The ratio of prM to E protein was measured by capture of VLP onto plates coated with DENV-2 immuned rabbit serum and DENV-2 E protein was measured by ELISA with MAb 3H5 (specific for DENV-2 domain III) and prM protein by mAb 155-49 (specific for DENV prM). The ratio was calculated as absorbance for prM/absorbance for E protein. The prM-uncleaved VLP (pucD2VLP), which contained the amino acid mutation at P1 and P2 sites from amino acid residue R/K to T/S (L. Li et al., *Science* 319, 1830 (2008)), respectively, was used as a standard to calculate the percentage of prM cleavage. Percent cleavage of prM was then calculated with reference to pucD2VLP, which was assumed to be 100% uncleaved as previously described (W. Dejnirattisai et al., *Nat Immunol* 16, 170 (2015)).

Antigen-capture ELISA was performed to quantify the amount of different VLP antigens. Briefly, flat-bottom 96-well MaxiSorp™ NUNC-Immuno plates (NUNC™, Roskilde, Denmark) were coated with 50 μL of rabbit anti-DENV-2 VLP serum at 1:500 in carbonate buffer (0.015 M $Na_2CO_3$, 0.035 $NaHCO_3$, pH 9.6), incubated overnight at 4° C., and wells were blocked with 200 μL of 1% BSA in PBS (1% PBSB) for 1 h at 37° C. Clarified antigens after harvest were titrated two-fold in PBSB and 50 μL were added to wells in duplicate, incubated for 2 h at 37° C., and washed 5 times with 200 μL of PBS with 0.1% Tween-20 (0.1% PBST). Normal COS-1 tissue culture fluid and cell pellets were used as control antigens. Captured antigens were detected by adding 50 μL of anti-DENV-2 MHIAF at 1:2,000 in blocking buffer, incubated for 1 h at 37° C., and washed 5 times. Fifty microliters of HRP-conjugated goat anti-mouse IgG (Jackson ImmunoResearch, Westgrove, Pa., USA) at 1:5,000 in blocking buffer were added to wells and incubated for 1 h at 37° C. to detect MHIAF. Subsequently, plates were washed 10 times. Bound conjugate was detected with 3,3',5,5'-tetramethylbenzidine substrate (Enhanced K-Blue® TMB, NEOGEN® Corp., Lexington, Ky., USA), incubated at room temperature for 10 min, and stopped with 2N $H_2SO_4$. Reactions were measured at $A_{450}$ using Sunrise™ TECAN microplate reader (Tecan, Grödig, Austria). The capability of antigen-capture ELISA in detecting pucD2VLP or pacD2VLP was titrated against purified D2VLP under known total protein concentration from individual preparation.

Total IgG ELISA was used to assay the presence of antigen-specific total IgG in the post-vaccination mice sera with the same antigen-capture ELISA protocol described above with minor modifications. Equal amounts of antigens were used determining from the standard curves using purified antigens by using a sigmoidal dose-response equation in GraphPad Prism version 6.0 (GraphPad Software, Inc., La Jolla, Calif., USA). Pooled sera from mice with the same immunization schedule, initially diluted at 1:1,000, were titrated two-fold and added to wells in duplicate and incubated for 1 h at 37° C. Pre-vaccination mice sera were included as negative controls. Incubations with conjugate and substrate were carried out according to the standard Ag-capture ELISA as above. $OD_{450}$ values were modeled as non-linear functions of the log 10 serum dilutions using a sigmoidal dose-response (variable slope) equation and endpoint antibody titers, from two independent experiments, were determined as the dilutions where the OD value was twice the average OD of negative control.

Epitope-blocking ELISA was performed to determine the vaccinated mouse response to the prM protein. The setup was similar to total IgG ELISA wherein plates were coated with rabbit anti-DENV-2 VLP serum, blocked with 1% BSA in PBS. After washing, pooled sera were diluted 1:40 in blocking buffer and incubated with pucD2VLP antigen (pre-titrated to OD 1.0) for 1 h at 37° C. After serum incubation and washing, a 1:4,000 dilution of MAb 155-49 conjugated with biotin by EZ-Link Sulfo-NHS-Biotin (ThermoFisher, Calif.) were added to each well and incubated for 1 h at 37° C. to compete with the already bound antibody from the immune mice sera for the DENV-2 VLP antigen. Bound conjugate was detected with 1:1000 HRP-conjugated streptavidin (016-030-084, Jackson ImmunoResearch) and incubated for 1 h at 37° C. After thorough washing with PBS for 10 times, TMB substrate was added into the wells and the plates were incubated for 10 min and stopped with 2N $H_2SO_4$. Reactions were measured at $A_{450}$. Percent blocking was determined by comparing replicate wells with Biotin-conjugated MAb competing against pre-adsorbed naïve mouse serum using the formula: % Blocking=[1-(OD of immune serum–OD of pre-immune serum)/(OD of biotin-conjugated MAb–OD of pre-immune serum)]×100.

Binding-ELISA was used to assess the binding activity of MAbs or mice immuned sera on D2VLP and mutant antigens using the same setup to antigen-capture ELISA protocol as described above with the exception that twofold dilutions of the specific MAb or immuned mice sera replaced the anti-DENV-2 MHIAF. Both D2VLP antigens were standardized to be equal quantity as determined by using purified D2VLP. The antibody endpoint reactivity was determined as for determining the endpoint antigen secretion titers.

SDS-PAGE and Western blotting

5 µg proteins of purified VLPs were mixed with 5 µl sample buffer and separated by 12% Tricine-sodium dodecyl sulfate-polyacrylamide gel electrophoresis (Tricine-SDS-PAGE) (H. Schägger, Nat Protoc 1, 16 (2006)). For immunodetection, proteins were blotted from gels onto NC membranes (IB23002, iBlot®2NC mini stacks, ThermoFisher Scientific) with iBlot® 2 Gel Transfer Device (IB21001, ThermoFisher Scientific). After incubation for 1 hour at room temperature in phosphate-buffered saline (pH 7.4) containing 5% skim milk (Cat No. 232100, BD biosciences, CA) to block nonspecific binding, membranes were cut into three at 40 kDa and 15 kDa band of protein marker (26616, ThermoFisher Scientific) for individually staining E, prM and P proteins by using anti-DENV2 MHIAF at 1:2000, anti-DENV prM MAb 155-49 at 0.5 µg/ml and mouse anti-M sera at 1:25, respectively at 4° C. overnight. Membranes were then washed three times for 15 min each, and specifically bound immunoglobulin was recognized with HRP-labeled goat anti-mouse IgG (Cat No: 115-035-146, Jackson ImmunoReasearch, Pa.) and was visualized with ECL (Cat No: RPN2235, GE Healthcare, UK) according to the manufacturer's protocol. The signals were detected by ImageQuant™ LAS 4000 mini (GE Healthcare). However, M protein were visualized with TMB membrane peroxidase substrate (Cat No: 50-77-03, KPL, Md.) to avoid high background from ECL.

Mouse Experiment

This study was carried out in compliance with the guidelines for the care and use of laboratory animals of the National Laboratory Animal Center, Taiwan. The animal use protocol has been reviewed and approved by the Institutional Animal Care and Use Committee (IACUC) of National Chung Hsing University (Approval Number: 101-58). All efforts were made to minimize suffering of mice. Groups of four 4-week-old female BALB/c mice were injected intramuscularly with pucD2VLP and pacD2VLP at weeks 0 and 4 at a dose of 4 µg/100 µL in PBS divided between the right and left quadriceps muscle. Mice were bled from the retro-orbital sinus before immunization and 4, 8, 12 weeks following the second injection, and individual mouse serum were evaluated for DENV-2 specific antibodies by ELISA and FRµNT as described in the following section. Pooled sera from each group of mice for prM-specific and E dimer-specific antibodies were used due to limited volume of mouse serum.

Virus Neutralization

The neutralizing ability of the immune mice sera against a number of representative DENV-2 genotype strains was measured by focus-reduction micro-neutralization test (FRµNT) as previously described. Briefly, $2.475 \times 10^4$ Vero cells/well were seeded into flat-bottom 96-well Costar cell culture plates (Corning Inc., Corning, N.Y., USA) and incubated 16 h overnight at 37° C. with 5% $CO_2$. Pooled sera were initially diluted at 1:10, heat-inactivated for 30 min at 56° C., titrated two-fold to a 40 µL volume, and 320 pfu/40 µL of DENV-1 to 4 was added to each dilution. The mixtures were then incubated for 1 h at 37° C. After incubation, 25 µL of the immune complexes were inoculated in duplicate into plates containing Vero cell monolayer. Plates were incubated for 1 h at 37° C. with 5% $CO_2$ and rocked every 10 min to allow infection. Overlay medium containing 1% methylcellulose (Sigma-Aldrich Inc., St. Louis, Mo., USA) in DMEM with 2% FBS was added and plates were incubated at 37° C. with 5% $CO_2$. Forty-eight hours later, plates were washed, fixed with 75% acetone in PBS and air-dried. Immunostaining was performed by adding serotype-specific MHIAF at 1:600 in 5% milk in 0.1% PBST and incubated for 60 min at 37° C., washing and adding goat anti-mouse IgG-HRP at 1:100 in 5% milk in 0.1% PBST and incubated for 45 min at 37° C. Infection foci were visualized using peroxidase substrate kit Vector® VIP SK-4600 (Vector Laboratories, Inc., Burlingame, Calif., USA) following the manufacturer's instructions. FRµNT titers were calculated for each virus relative to a virus only control back-titration. Titers of exact 50% reduction of infection foci (FRµNT50) were modeled using a sigmoidal dose-response (variable slope) formula. All values are taken from the average of two independent experiments. Target viruses were: DENV-1, strain Hawaii; DENV-2, strain 16681; DENV-3, strain H87; and DENV-4, strains H241. In the calculation of geometric mean titer (GMT) for graphic display and statistical analysis, a FRµNT50 titer of <10 was represented with the value of 1 and 5, respectively.

Generating Hybridoma and Mab Screening

Hybridoma secreting anti-DENV antibodies were generated from the pacD2VLP immunized mice according to a standard procedure (Kohler et al, 1975), with slight modifications (Chen et al, 2007). First, the pacD2VLP immunized mouse will be boosted with another 4 ug of pacD2VLP before sacrifice. On day 4 after the final boost, splenocytes will be harvested from the immunized mouse spleen and fused with NSI/I-Ag4-1 myeloma cells using antibody delivery kit (GenomONE™-CF HVJ Envelope Cell Fusion Kit, Gosmo Bio Co, ISK10 MA17). Fused cell pellet will be resuspended in DMEM supplemented with 15% FBS, hypoxanthine-aminopterin-thymidine medium, and hybridoma cloning factor (ICN, Aurora, Ohio). Hybridoma colonies were screened for secretion of MAbs by antigen-capture ELISA as described above. The C6/36 culture supernatant of DENV-2 virus was used at standardized OD 1.0 and the MHIAF was replaced by culture supernatant from each of the hybridoma colonies. Selected positive clones were subcloned by limiting dilution. Ascitic fluids were produced in pristane-primed BALB/c mice. Hybridoma cell lines were grown in DMEM with 10% heat inactivated FBS. MAbs were affinity purified with protein G Sepharose 4B gel and the amount of purified MAbs were quantified by comparing with the amount of standard IgG with ELISA.

Profiling of prM/E-Specific Ig Genes from a Single B-Cell

Ig genes from a single B cell were isolated essentially following the protocols established by previous reports with some modifications. Briefly, single cell suspension was collected from the spleens of BALB/c mice immunized i.m. two times at 4 weeks apart with pucD2VLP and pacD2VLP. The D2VLP(+), B220 (+) and IgG1(+) splenic B cells were isolated by flow cytometry (FACSAria II), and the single B cell was sorted into 96-well PCR plates containing 4 ul/well of ice-cold RNase-free water supplemented with 10 mM DTT and 3U RNase inhibitor (Promega). RT-PCR reactions were performed using the Qiagen OneStep RT-PCR kit (Qiagen) at 50° C. 30 min and then 95° C. for 15 min followed by 40 cycles of 95° C. for 1 min, 55° C. for 1 min and 72° C. 1 min, and final incubation at 72° C. for 5 min, with the primers as described previously. The nested PCR was performed with 2 ul of unpurified first-round PCR product at 95° C. for 1 min followed by 40 cycles of 95° C. 30 sec, 57° C. (IgH) or 45° C. (Igk) or 55° C. (Igλ) for 30 sec, 72° C. for 45 sec and incubated at 72° C. for 10 min as previously described. Aliquotes of nested PCR products were sequenced and analyzed using IMGT/V-Quest (www_imgt_org) to identify the highest homology gene loci of germ-line V, D and J genes. Ig genes were then translated and aligned by CLUSTALW to define the clonally amplified Ig genes.

CryoEM and 3D Reconstruction

Figure 6:
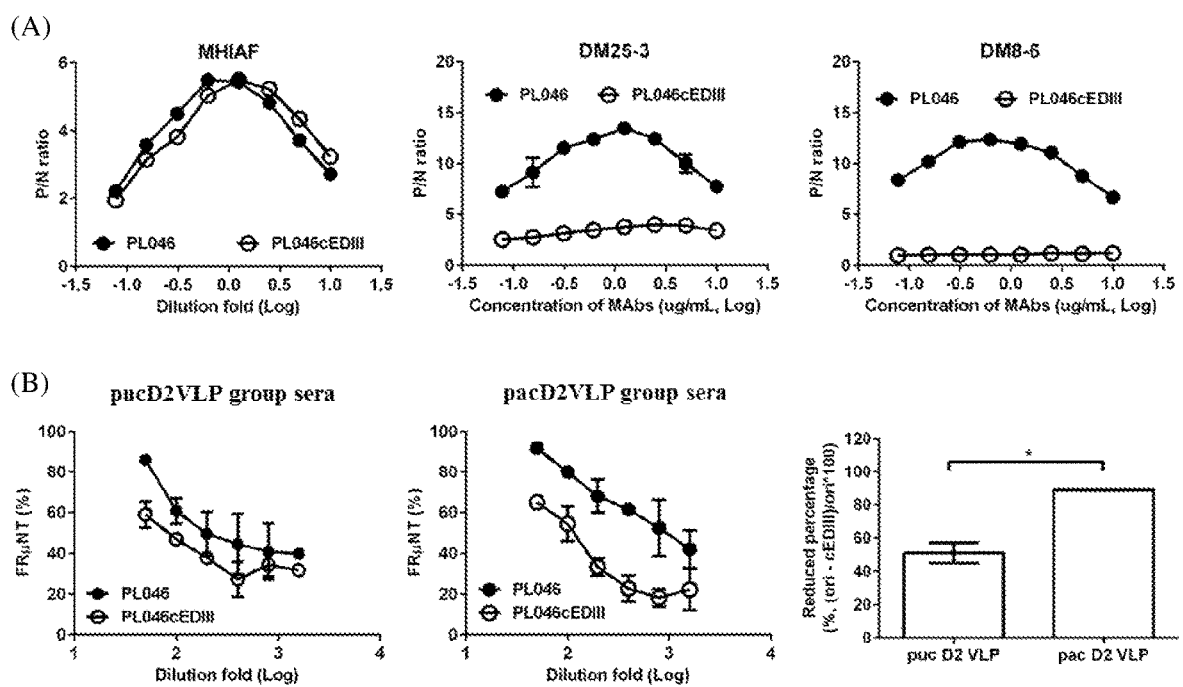
FIG. 6 shows the characterization of DM25-3 binding to the quaternary epitope by using a domain III replaced DENV-2 recombinant virus. (A) A recombinant DENV-2 was produced by replacing domain III with consensus domain III (PL046cEDIII) and the results of binding-ELISA from both parental DENV-2 strain PL046 and PL046cEDIII was compared. DENV-2 MHIAF showed similar binding to both viruses (left). Significant loss of binding to DENV-2 of DM 25-3 was observed when domain III was removed (middle). Since DM8-6 recognized epitope located at domain III, loss of binding of DM8-6 to PL046cEDIII was served as positive control when domain III was removed (right). (B) showed the 50% antigen focus-reduction micro neutralization titers (FRμNT50) of the post-immunized mice sera from both pacD2VLP and pucD2VLP immunized mice on both PL046 and PL046cEDIII DENV-2 viruses. The difference in FRμNT50 from both pacD2VLP and pucD2VLP immunization groups were converted to bar chart at 1:1000 fold dilution of mice sera. The data are presented as the means+standard deviation (SD) from three independent experiments. *, $p<0.05$.

Freshly prepared dengue virus sample (~3 µl) was placed onto a glow-discharged Quatifoil 2/2 grid (Quatifoil GmbH, Germany), blotted with filter paper, and plunged into liquid nitrogen-cooled liquid ethane using Gatan CP3. CryoEM images were recorded with a JEOL2100F field emission gun transmission electron microscope using an accelerating voltage of 200 kV and a magnification of 15,000× on a direct electron detector (DE-12 Camera System—Direct Electron, LP) with a 6 µm pixel size (corresponding to ~4 Å at the specimen level). 4 Å/pixel. The measured defocus values of these images range from −2 µm to −4.5 µm. The imaging electron dosage was ~10 e−/Å$^2$. The image processes were performed by EMAN2 {Tang, 2007 #3}. The reconstruction process ended when there was no improvement achieved (FIG. 6). The resolution of the final reconstructions was estimated in EMAN2 from a Fourier shell correlation curve comparing two reconstructions from randomly chosen "odd" and "even" particles. The fsc curve dropped below 0.5 was used to estimate the resolution (FIG. 6). The cryoEM structure of DENV2 (PDB code: 3J27) was manually fitted into the DENV2 VLP density map using UCSF Chimera. Solvent accessible surface area (SASA) of individual amino acid molecule on pacD2VLP was calculated by POPS program (A. Fornili et al., *Methods Mol Biol* 819, 375 (2012)).

Statistical Analysis

All data are represented as means±standard error and analyzed using GraphPad Prism version 6.0. Unpaired t test was used to analyze data sets between two groups. Mann-Whitney U test to account for non-normality of some transformed data was also applied. P values<0.05 were considered significant.

REFERENCE

1. B. D. Lindenbach, C. M. Rice, Flaviviridae: The viruses and their replication, p. 991-1110. In D. M. Knipe and P. M. Howley (ed.) Fields' Virology, 4th ed. Lippincott Williams & Wilkins, Philadelphia, Pa., (2001).
2. S. Bhatt et al., The global distribution and burden of dengue. *Nature* 496, 504 (2013).
3. B. Guy, N. Jackson, Dengue vaccine: hypotheses to understand CYD-TDV-induced protection. *Nat Rev Microbiol* 14, 45 (2016).
4. A. Wilder-Smith, D. Gubler, PUBLIC HEALTH. Dengue vaccines at a crossroad. *Science* 350, 626 (2015).
5. L. Li et al., The flavivirus precursor membrane-envelope protein complex: structure and maturation. *Science* 319, 1830 (2008).
6. V. Kostyuchenko, Q. Zhang, J. Tan, T. Ng, S. Lok, Immature and mature dengue serotype 1 virus structures provide insight into the maturation process. *J Virol* 87, 7700 (2013).
7. T. Pierson, M. Diamond, Degrees of maturity: the complex structure and biology of flaviviruses. *Curr Opin Virol* 2, 168 (2012).
8. J. Junjhon et al., Influence of pr-M cleavage on the heterogeneity of extracellular dengue virus particles. *J Virol* 84, 8353 (2010).
9. W. Dejnirattisai et al., Cross-reacting antibodies enhance dengue virus infection in humans. *Science* 328, 745 (2010).
10. I. Rodenhuis-Zybert et al., Immature dengue virus: a veiled pathogen? *PLoS Pathog* 6, e1000718 (2010).
11. S. Nelson et al., Maturation of West Nile virus modulates sensitivity to antibody-mediated neutralization. *PLoS Pathog* 4, e1000060 (2008).
12. S. Allison, K. Stadler, C. Mandl, C. Kunz, F. Heinz, Synthesis and secretion of recombinant tick-borne encephalitis virus protein E in soluble and particulate form. *J Virol* 69, 5816 (1995).
13. J. Schalich et al., Recombinant subviral particles from tick-borne encephalitis virus are fusogenic and provide a model system for studying flavivirus envelope glycoprotein functions. *J Virol* 70, 4549 (1996).
14. I. Ferlenghi et al., Molecular organization of a recombinant subviral particle from tick-borne encephalitis virus. *Mol Cell* 7, 593 (2001).
15. T. Chambers, D. McCourt, C. Rice, Production of yellow fever virus proteins in infected cells: identification of discrete polyprotein species and analysis of cleavage kinetics using region-specific polyclonal antisera. *Virology* 177, 159 (1990).
16. M. Crabtree, R. Sang, V. Stollar, L. Dunster, B. Miller, Genetic and phenotypic characterization of the newly described insect flavivirus, Kamiti River virus. *Arch Virol* 148, 1095 (2003).
17. J. Junjhon et al., Differential modulation of prM cleavage, extracellular particle distribution, and virus infectivity by conserved residues at nonfurin consensus positions of the dengue virus pr-M junction. *J Virol* 82, 10776 (2008).
18. P. Keelapang et al., Alterations of pr-M cleavage and virus export in pr-M junction chimeric dengue viruses. *J Virol* 78, 2367 (2004).
19. S. Tian, W. Huajun, J. Wu, Computational prediction of furin cleavage sites by a hybrid method and understanding mechanism underlying diseases. *Sci Rep* 2, 261 (2012).
20. W. Crill, H. Hughes, M. Delorey, G. Chang, Humoral immune responses of dengue fever patients using epitope-specific serotype-2 virus-like particle antigens. *PLoS One* 4, e4991 (2009).
21. Z. Wang et al., Obstruction of dengue virus maturation by Fab fragments of the 2H2 antibody. *J Virol* 87, 8909 (2013).
22. W. Dejnirattisai et al., A new class of highly potent, broadly neutralizing antibodies isolated from viremic patients infected with dengue virus. *Nat Immunol* 16, 170 (2015).
23. A. Rouvinski et al., Recognition determinants of broadly neutralizing human antibodies against dengue viruses. *Nature* 520, 109 (2015).
24. J. Aaskov, H. Geysen, M. T J, Serologically defined linear epitopes in the envelope protein of dengue 2 (Jamaica strain 1409). *Arch Virol* 105, 209 (1989).
25. X. Zhang et al., Cryo-EM structure of the mature dengue virus at 3.5-Å resolution. *Nat Struct Mol Biol* 20, 105 (2013).
26. R. J. Kuhn et al., Structure of dengue virus: implications for flavivirus organization, maturation, and fusion. *Cell* 108, 717 (2002).
27. W. Tsai et al., High-avidity and potently neutralizing cross-reactive human monoclonal antibodies derived from secondary dengue virus infection. *J Virol* 87, 12562 (2013).

28. S. M. Lok et al., Binding of a neutralizing antibody to dengue virus alters the arrangement of surface glycoproteins. *Nat Struct Mol Biol* 15, 312 (2008).

29. G. Fibriansah et al., DENGUE VIRUS. Cryo-EM structure of an antibody that neutralizes dengue virus type 2 by locking E protein dimers. *Science* 349, 88 (2015).

The invention claimed is:

1. An expression vector, encoding a Dengue virus (DENV) virus-like particle having a membrane protein; wherein said membrane protein comprises a DENV pr-M junction of SEQ ID NO: 49 at its pre-cleaved form.

2. The expression vector of claim 1, wherein said DENV pr-M junction comprises SEQ ID NO: 5, SEQ ID NO: 9, or SEQ ID NO: 13.

3. The expression vector of claim 1, wherein said expression vector comprises SEQ ID NO: 16.

4. A Dengue virus (DENV) virus-like particle, comprising a membrane protein; wherein said membrane protein comprises a DENV pr-M junction of SEQ ID NO: 49 at its pre-cleaved form.

5. The virus-like particle of claim 4, wherein said DENV pr-M junction comprises SEQ ID NO: 5, SEQ ID NO: 9, or SEQ ID NO: 13.

6. A composition, comprising said Dengue virus (DENV) virus-like particle of claim 4 and a pharmaceutically acceptable carrier or a pharmaceutically acceptable adjuvant.

7. The composition of claim 6, wherein said DENV pr-M junction comprises SEQ ID NO: 5, SEQ ID NO: 9, or SEQ ID NO: 13.

8. The composition of claim 6, wherein said pharmaceutically acceptable carrier comprises water, mannitol, lactose, starch, magnesium stearate, or combination thereof.

9. The composition of claim 6, wherein said pharmaceutically acceptable adjuvant comprises an aluminum adjuvant, an oil-in-water type suspension adjuvant containing squalene, a ligand of Toll-like receptor, a saponin-based adjuvant, a polymer-based adjuvant, or a combination thereof.

* * * * *